(12) United States Patent
Verness

(10) Patent No.: US 6,785,576 B2
(45) Date of Patent: *Aug. 31, 2004

(54) MEDICAL ELECTRICAL LEAD

(75) Inventor: David D. Verness, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 207 days.

This patent is subject to a terminal disclaimer.

(21) Appl. No.: 10/106,669

(22) Filed: Mar. 25, 2002

(65) Prior Publication Data

US 2002/0099430 A1 Jul. 25, 2002

Related U.S. Application Data

(60) Continuation-in-part of application No. 09/616,592, filed on Jul. 14, 2000, which is a division of application No. 09/482,775, filed on Jan. 13, 2000, now Pat. No. 6,119,042, which is a division of application No. 09/247,324, filed on Feb. 10, 1999, now Pat. No. 6,061,598, which is a division of application No. 09/070,171, filed on Apr. 30, 1998, now Pat. No. 6,018,683, which is a division of application No. 08/843,763, filed on Apr. 21, 1997, now Pat. No. 6,285,910.

(51) Int. Cl.[7] .................................................. A61N 1/05
(52) U.S. Cl. .................................................... 607/122
(58) Field of Search ................................ 607/116, 119, 607/122–128; 600/373–381

(56) References Cited

U.S. PATENT DOCUMENTS

| | | |
|---|---|---|
| 3,474,791 A | 10/1969 | Bentov |
| 3,572,344 A | 3/1971 | Bolduc |
| 3,844,292 A | 10/1974 | Bolduc |
| 4,033,355 A | 7/1977 | Amundson |
| 4,559,951 A | 12/1985 | Dahl et al. |
| 4,572,608 A | 2/1986 | Mochizuki et al. |
| 4,577,643 A | 3/1986 | Beranek |
| 4,934,049 A | 6/1990 | Kiekhafer et al. |
| 4,972,848 A | 11/1990 | Di Domenico et al. |
| 5,231,996 A | 8/1993 | Bardy et al. |
| 5,545,203 A | 8/1996 | Doan |
| 5,584,873 A | 12/1996 | Shoberg et al. |
| 5,591,142 A | 1/1997 | Van Erp |
| 5,649,967 A * | 7/1997 | De Bellis et al. ............... 607/9 |
| 5,676,694 A | 10/1997 | Boser et al. |
| 6,018,683 A | 1/2000 | Verness et al. |
| 6,026,567 A | 2/2000 | Swoyer et al. |
| 6,061,598 A | 5/2000 | Verness et al. |
| 6,119,042 A | 9/2000 | Verness et al. |
| 6,285,910 B1 | 9/2001 | Verness et al. |

* cited by examiner

*Primary Examiner*—Jeffrey R. Jastrzab
(74) *Attorney, Agent, or Firm*—Elisabeth L. Belden; Girma Wolde-Michael

(57) ABSTRACT

A temporary backup mechanism for electrical conduction within an implantable medical device (IMD) is provided. In an IMD such as lead or catheter having a cable conductor for conducting an electrical signal is provided with a safety cable for conducting an electrical signal if the primary cable conductor fails. In one embodiment, the conductor is a cable positioned adjacent to the safety cable so that the cable is in electrical contact with the conductor along various points on the conductor. In another embodiment, the conductor and cable are electrically isolated from one another except at proximal and distal ends where the two are mechanically coupled. In the latter embodiment, a change in impedance signals a potential conductor failure.

17 Claims, 22 Drawing Sheets

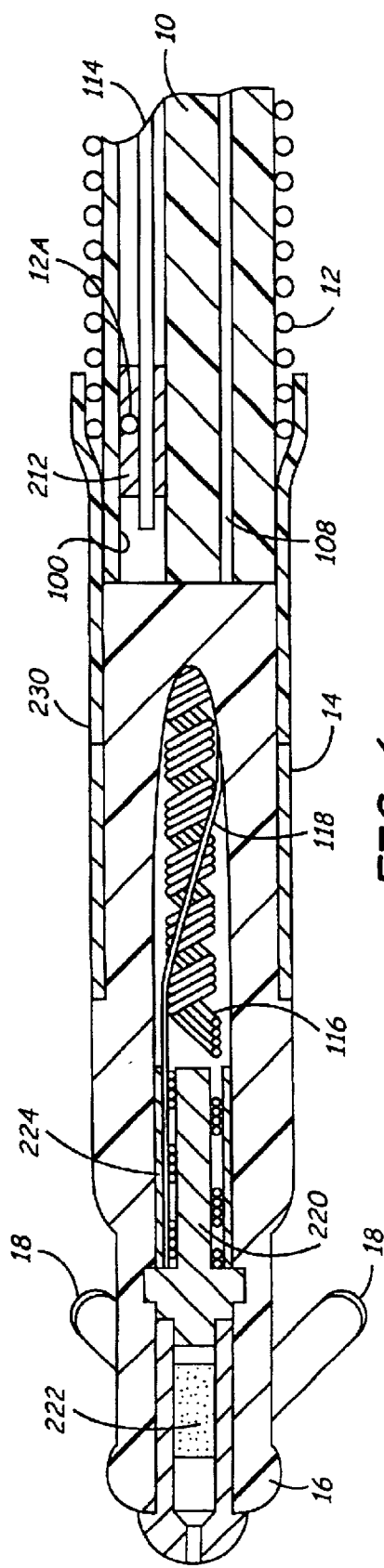
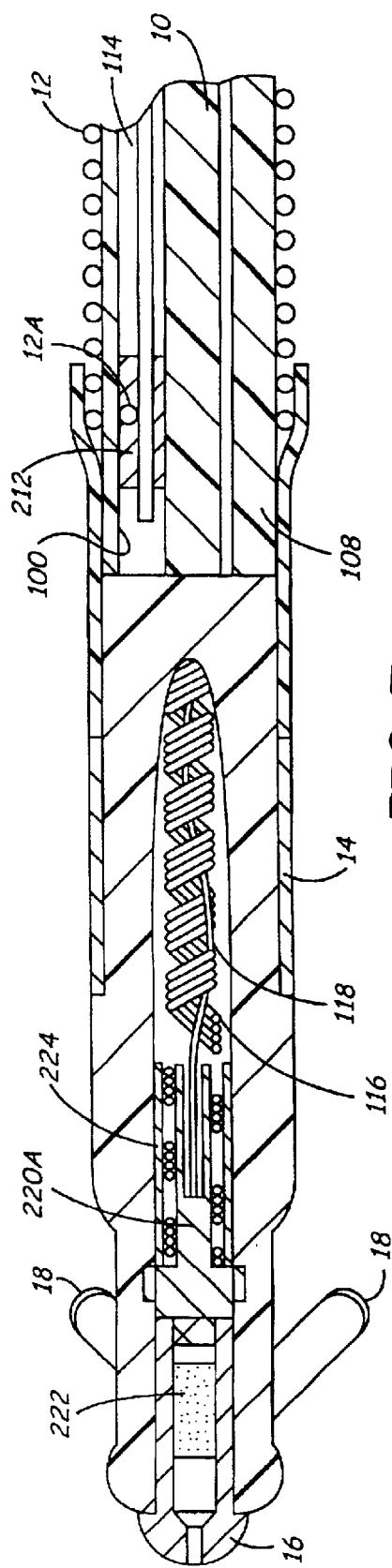
FIG. 6
FIG. 7

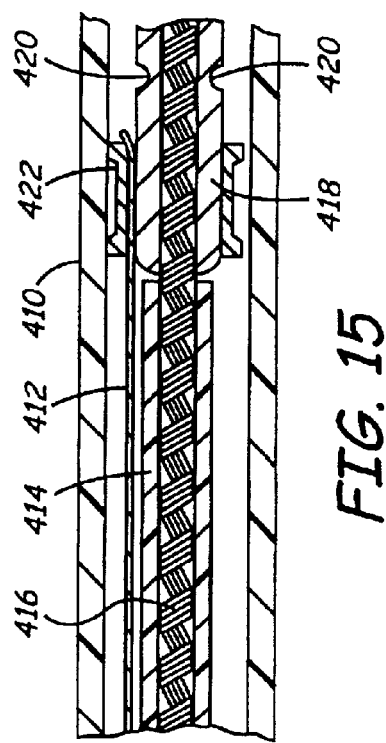
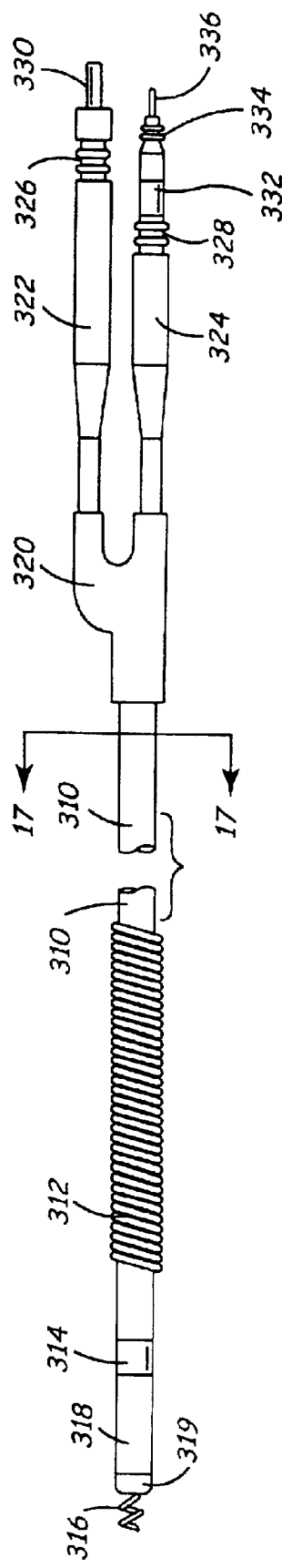

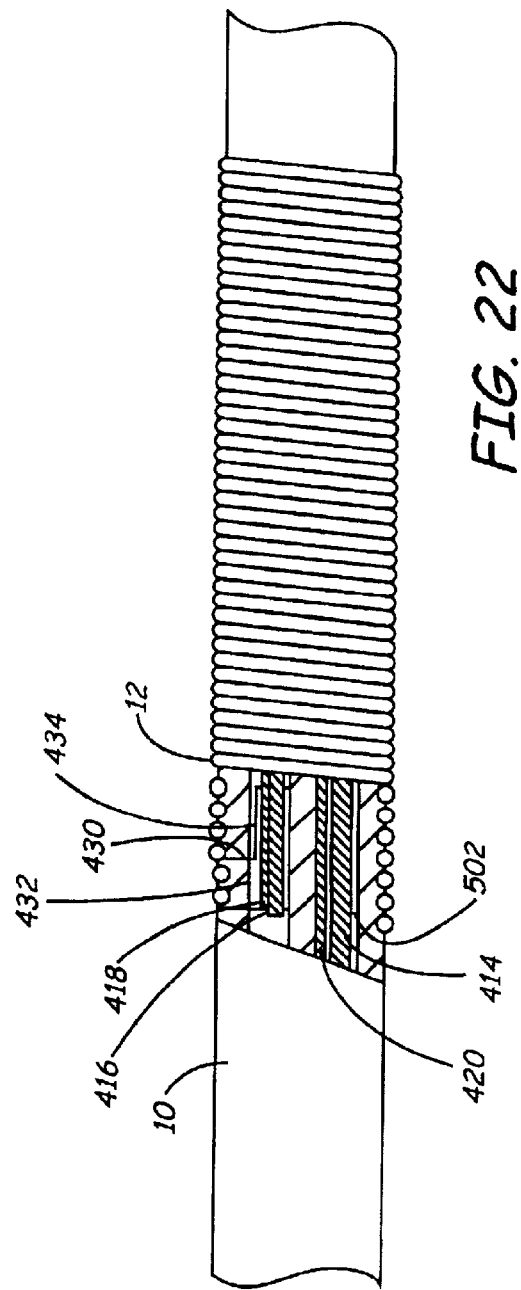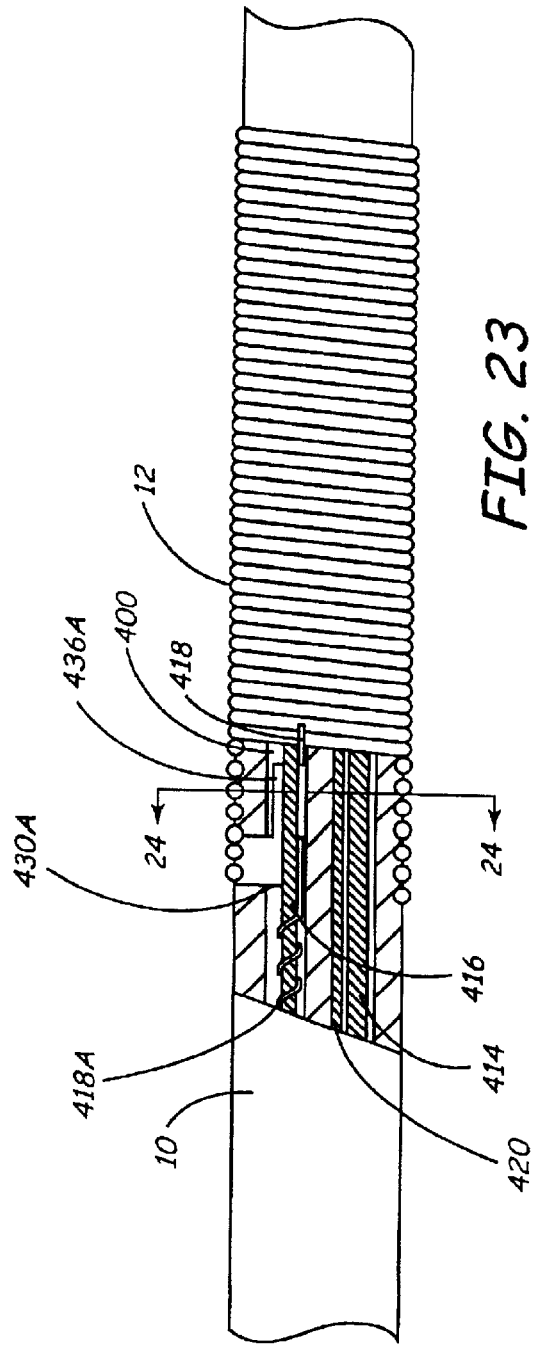

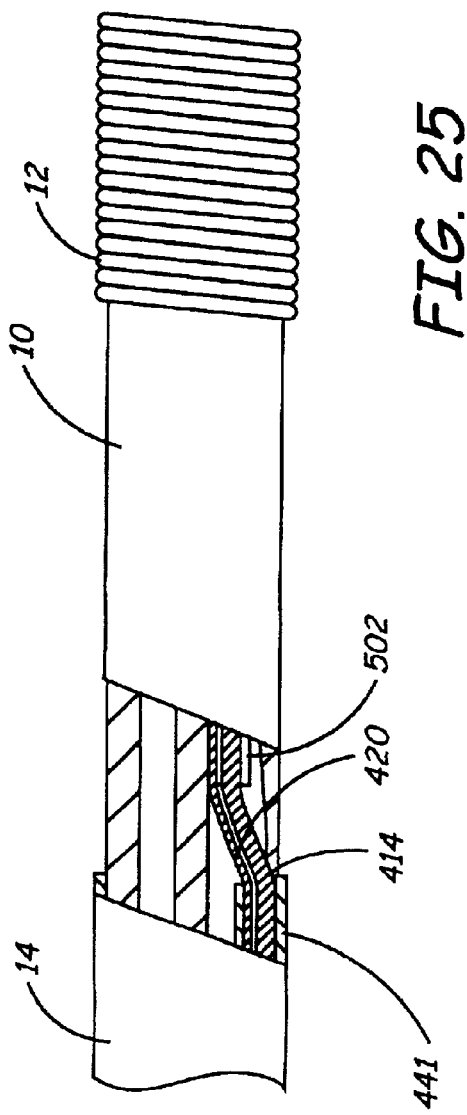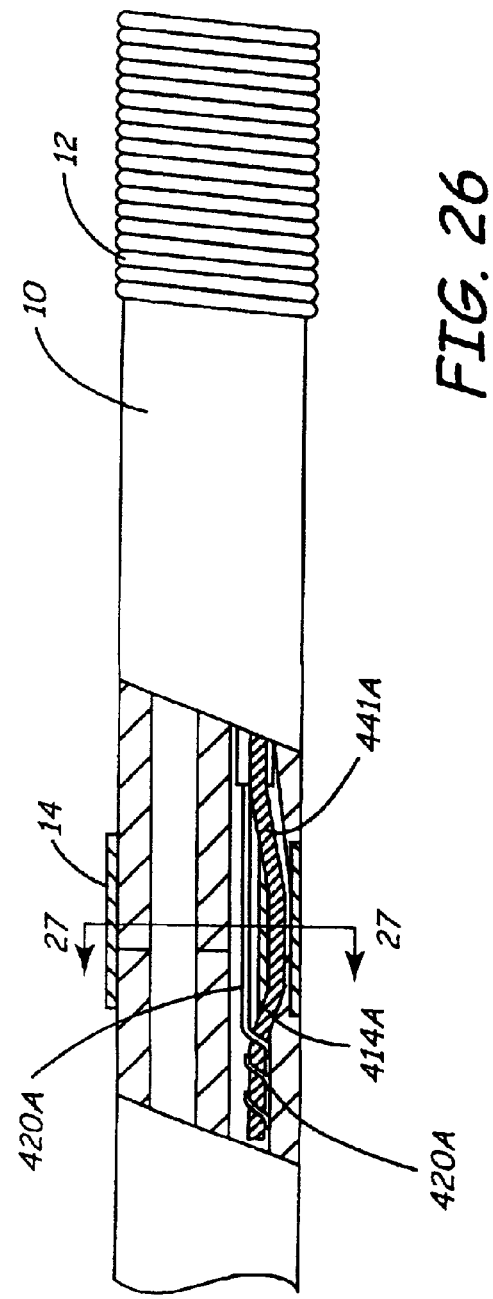

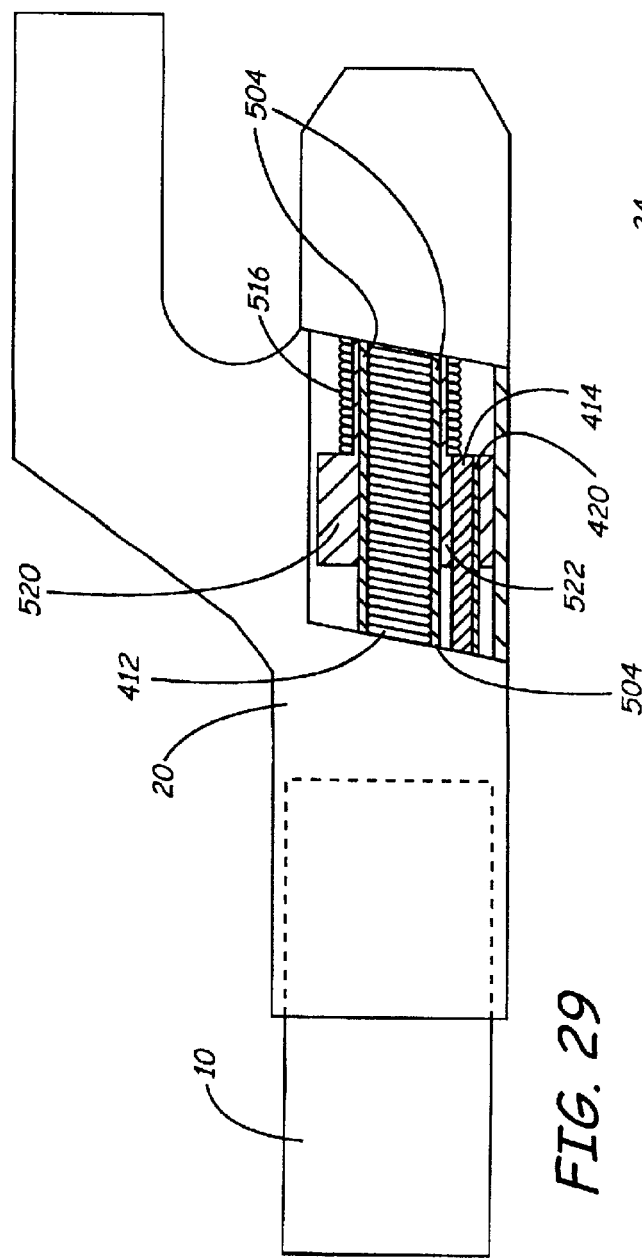
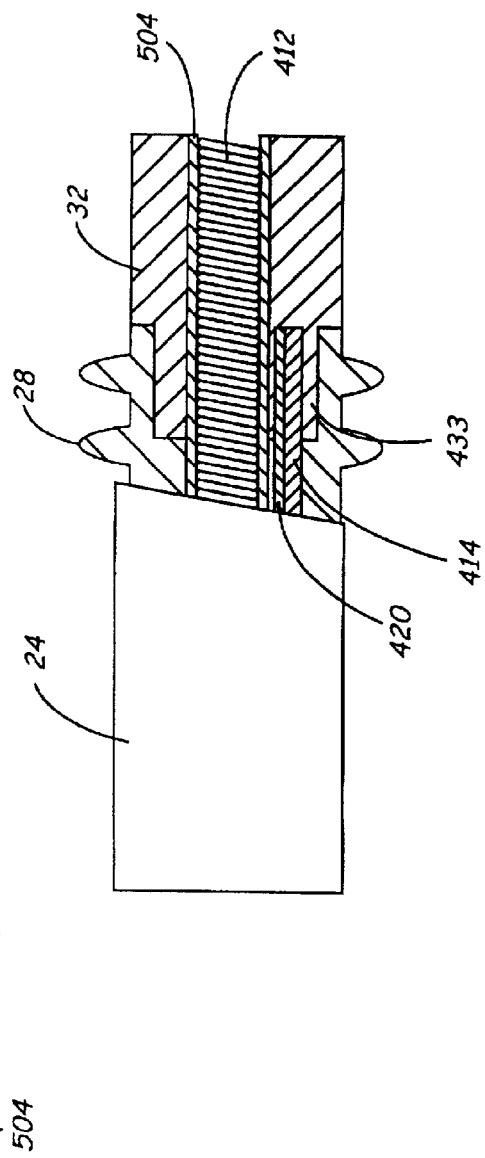
FIG. 29
FIG. 30

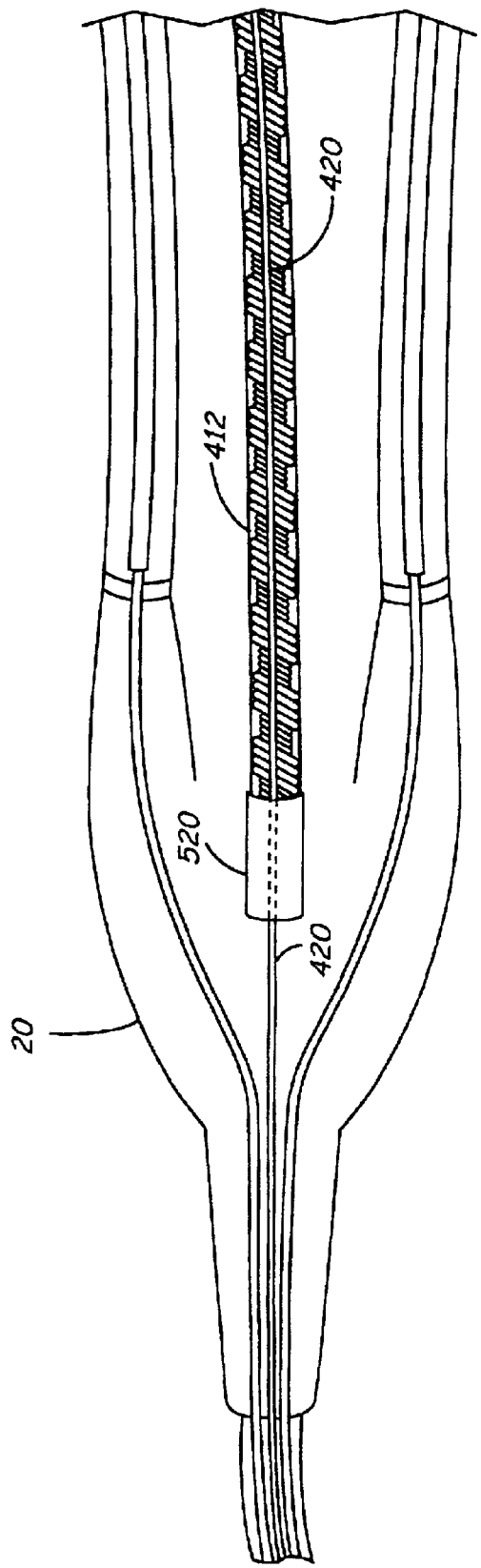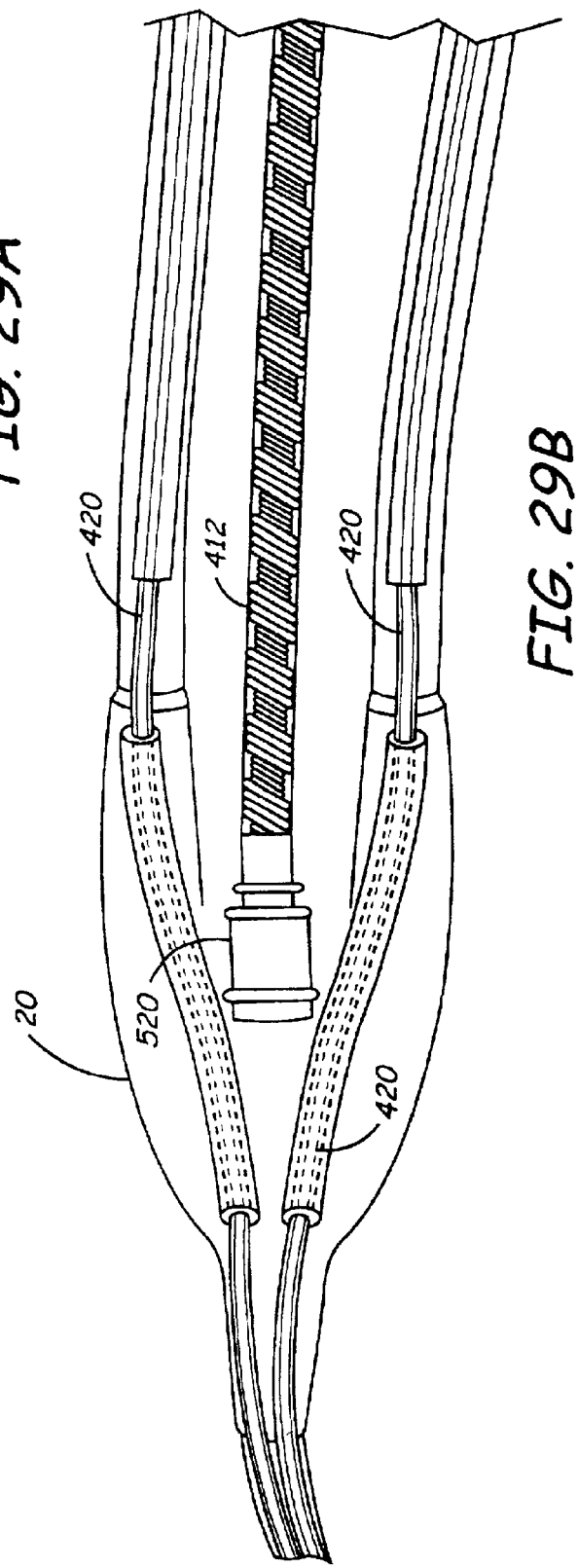

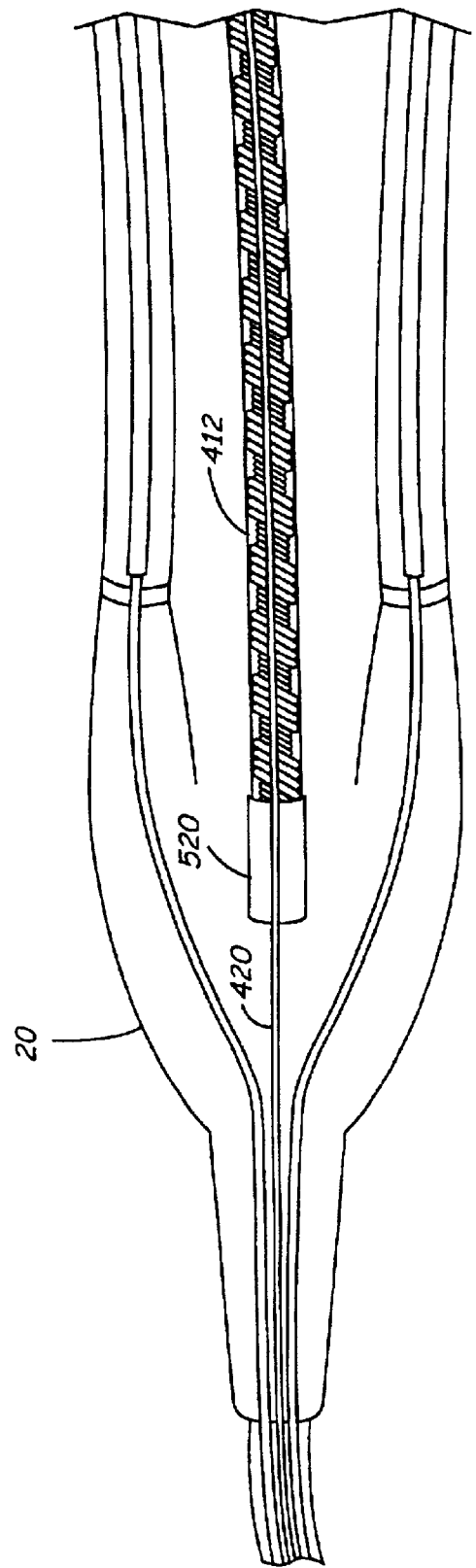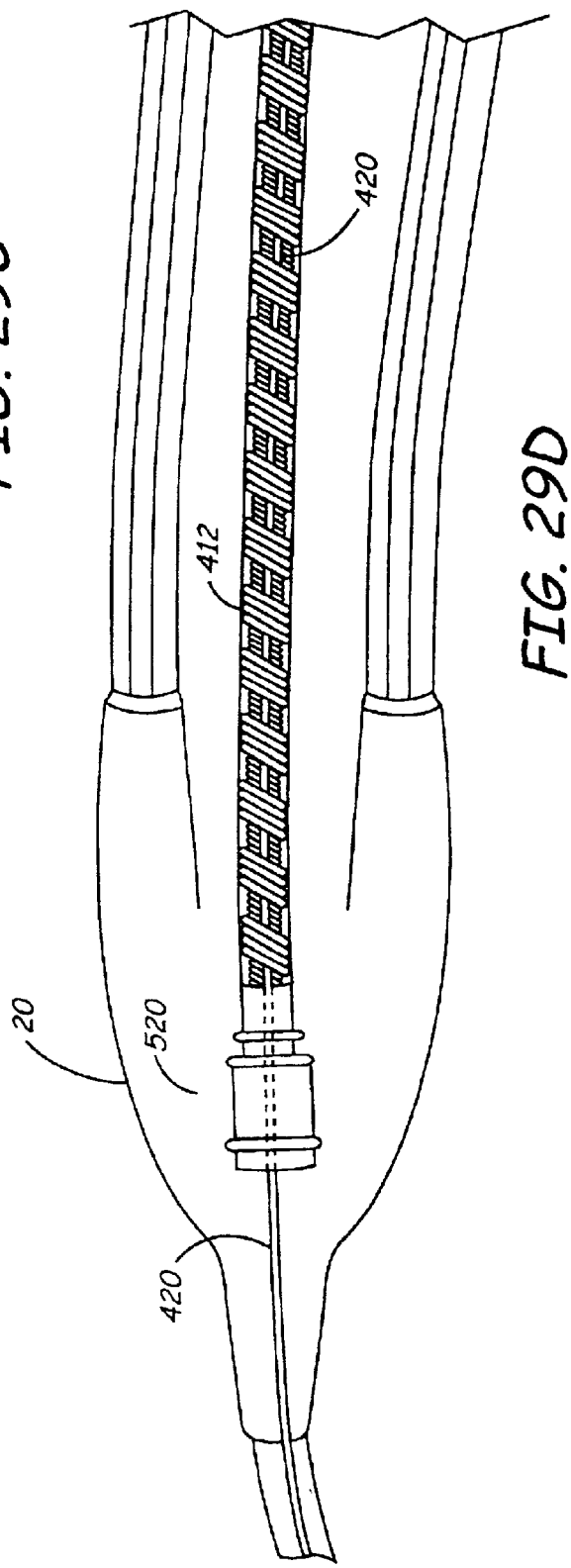

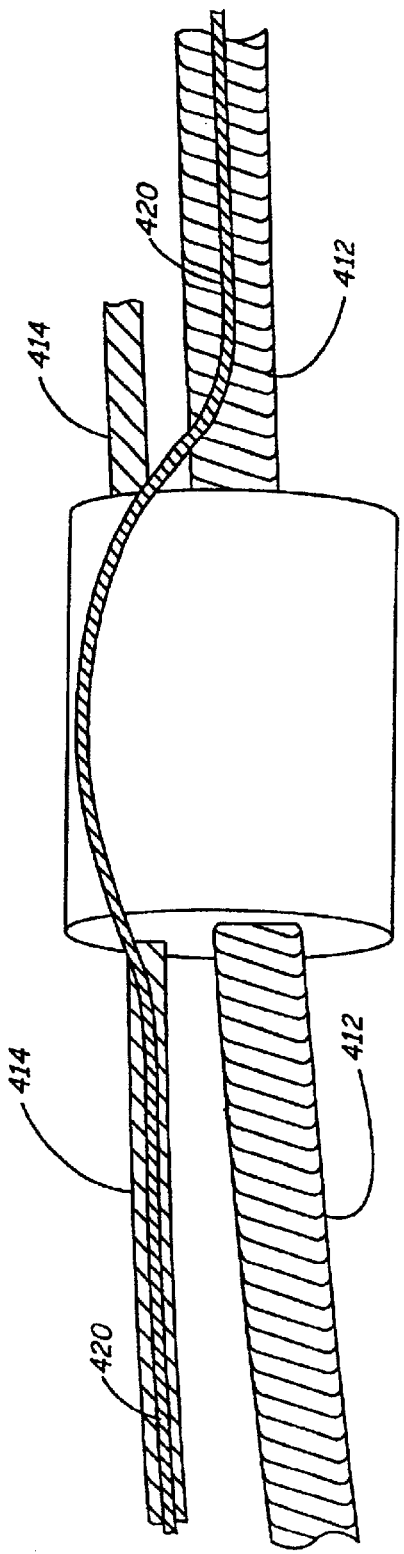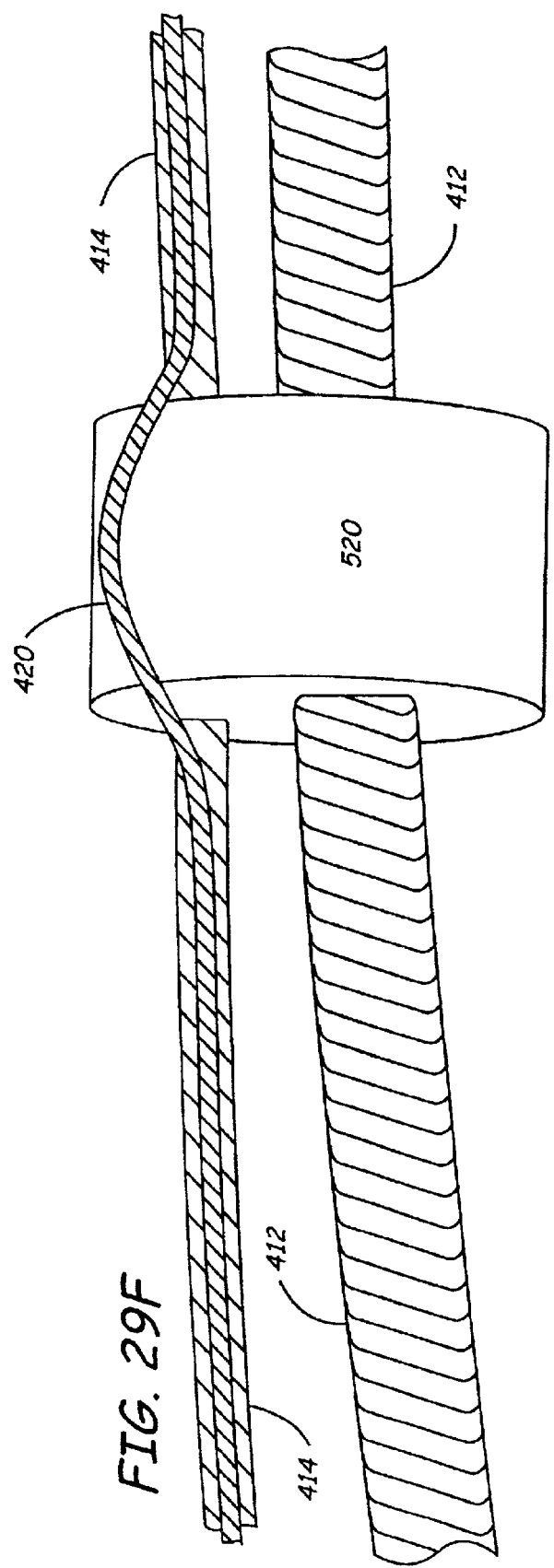

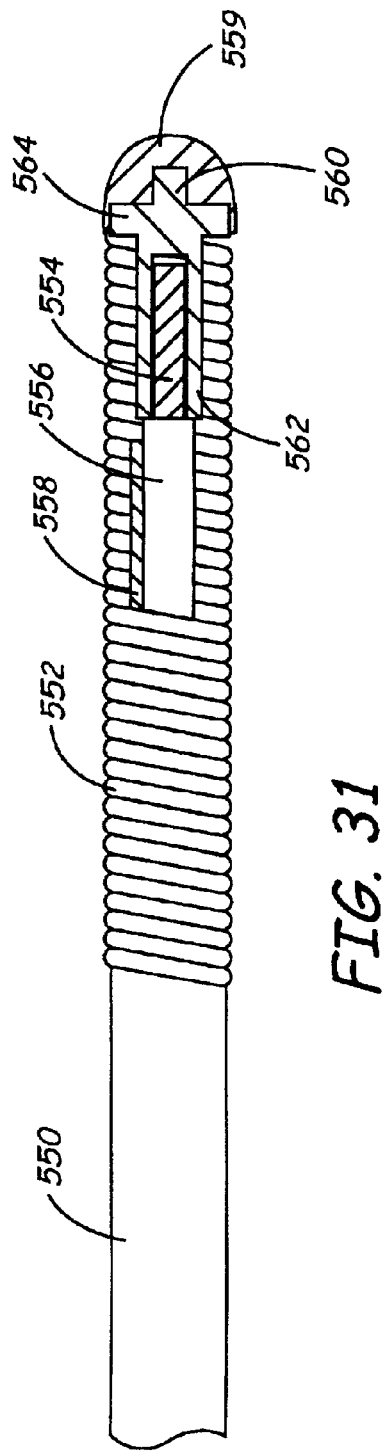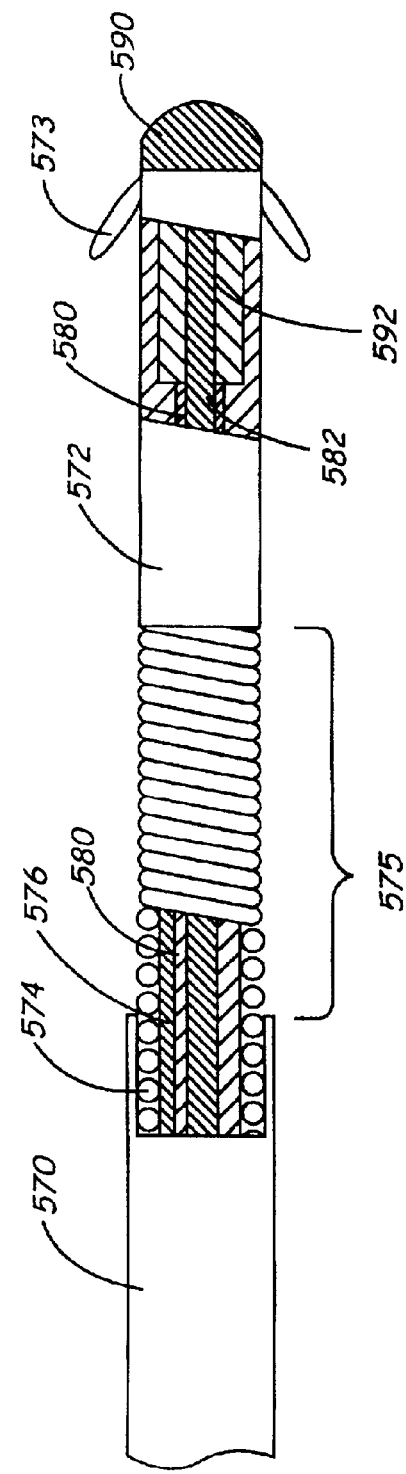

MEDICAL ELECTRICAL LEAD

RELATED APPLICATIONS

This application is a continuation-in-part of prior U.S. application Ser. No. 09/616,592 filed Jul. 14, 2000, which is a continuation of 09/482,775 filed Jan. 13, 2000 now U.S Pat. No. 6,119,042 granted Sep. 12, 2000, which is a divisional application of 09/247,324 filed Feb. 10, 1999 now U.S. Pat. No. 6,061,598 granted May 9, 2000, which is a divisional of 09/070,171 filed Apr. 30, 1998 now U.S Pat. No. 6,018,683 granted Jan. 25, 2000, which is a divisional of 08/843,763 filed Apr. 21, 1997 now U.S Pat. No. 6,285,910 granted Sep. 4, 2001.

FIELD OF THE INVENTION

The present invention relates to implantable electrical leads generally; and, more specifically, to cardiac pacing leads.

BACKGROUND OF THE INVENTION

The conductors in cardiac pacing leads occasionally have a tendency to fracture due to repetitive application of stress to the conductor. One way in which this problem has previously been addressed is by reinforcing the lead body in the area in which stress is to be expected, as in U.S. Pat. No. 5,545,203, issued to Doan et al. Reinforcement of the lead body is also disclosed in U.S. Pat. No. 5,591,142, issued to Van Erp et al. It has also been proposed to reinforce the lead body by means of adding a tensile reinforcement as in U.S. Pat. No. 5,231,996 issued to Bardy et al. In this patent, the lead is provided with a non-conductive tensile member such as a polyester cord, which runs the length of the lead body. Other leads having cords or reinforcements running throughout their length are disclosed in U.S. Pat. No. 3,844,292 and U.S. Pat. No. 3,572,344 issued to Bolduc. A third proposal for dealing with the possibility of conductor fracture is to render the portion of the lead body in direct contact with the conductor conductive by addition of carbon or other conductive material, as disclosed in U.S. Pat. No. 4,033,355, issued to Ammundson.

Despite prior efforts, an improved mechanism is needed to prevent failures of the conductive cables carried by lead bodies, wherein the failures are due to compressive forces.

SUMMARY OF THE INVENTION

The present invention is directed toward providing a temporary backup for electrical conduction in the event of a conductor failure within a lead. An implantable medical device (IMD) such as lead or catheter having a conductor for conducting an electrical signal includes a safety cable to provide a backup path for electrical current if the cable conductor fails. In one embodiment, the conductor is a cable positioned adjacent to the safety cable. In another embodiment, the IMD includes multiple coaxially configured coils, with a safety cable being positioned between an insulative layer adjacent the inner coil to provide redundancy for the outer coil.

According to one aspect of the invention, the safety cable may have a smaller diameter than the conductor cable. In this instance, the safety cable is designed to add as little as possible to the overall diameter of the lead body, but has enough cross section to adequately carry the electrical current required to temporarily maintain the function of the lead if the conductor cable should fail. The safety cable may be in electrical contact with the conductor along one or more portions of its length. Alternatively, the conductor and safety cable may be electrically insulated from one another except for connection points at the distal and proximal ends of the conductor. The latter embodiment allows for the detection of a failure in the conductor using impedance changes that occur in the lead after the failure occurs.

In one embodiment of the invention, the connections of the safety cable to the conductor need only assure intimate contact between the two cables for non-intermittent conduction of electricity and need not have the same mechanical integrity to withstand tensile loading as the rest of the lead body members. In addition, the safety cable may be assembled into the lead body free of residual tensile stress. In another embodiment, a lead might contain multiple conductors, each being associated with a respective safety cable.

BRIEF DESCRIPTION OF THE DRAWINGS

FIG. 6 is a side, cut-away view through the distal portion of the lead of FIG. 1, illustrating the first embodiment of the invention.

FIG. 7 is a side, cut-away view through the distal portion of the lead of FIG. 1, illustrating the second embodiment of the invention.

FIG. 15 is a side, cut-away view through the lead according to the present invention, illustrating an alternative mechanism for interconnecting a coiled conductor with a stranded conductor.

FIG. 16 is a plan view of a lead having a rotatable fixation helix, embodying the present invention.

FIG. 22 is a side cut-away view of a portion of a lead according to FIG. 20.

FIG. 23 is a side cut-away view of an alternative embodiment of the lead shown in FIG. 22.

FIG. 25 is a partial side cut-away view of a dual cable design showing the interconnection of a safety cable and low-voltage conductor cable at anode ring electrode.

FIG. 26 is a partial side cut-away view of a dual cable design showing an alternative mechanism for interconnecting safety cable and low-voltage conductor cable at an anode ring electrode.

FIG. 29 is a side cutaway view illustrating one manner of coupling the conductor cable to the safety cable within the bifurcation sleeve.

FIG. 30 is a side cutaway view illustrating another mechanism for coupling the conductor cable to the safety cable within the bifurcation sleeve.

FIG. 31 is a cut-away view illustrating one embodiment of a distal end of a unipolar implantable defibrillation lead in which the current invention may be practiced.

FIG. 32 is a cut-away view illustrating an embodiment of a distal end of a bipolar, coaxial implantable lead in which the current invention may be practiced.

DETAILED DESCRIPTION OF THE PREFERRED EMBODIMENTS

Figure 1:
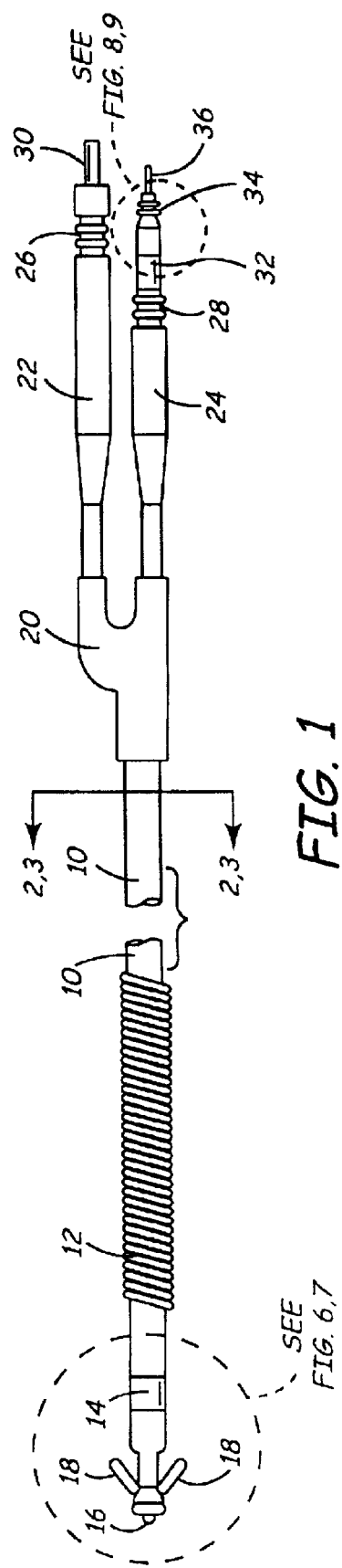
FIG. 1 is a plan view of an implantable lead in which the present invention is practiced.

FIG. 1 is a plan view of a defibrillation lead in which the present invention is practiced. The present invention may also be usefully practiced in the context of other types of medical electrical leads, such as cardiac pacing leads, nerve and muscle stimulation leads, and so forth.

The lead of FIG. 1 is provided with an elongated insulative lead body 10, preferably fabricated of silicone rubber, polyurethane or other biocompatible elastomers. The proximal end of the lead carries an elongated defibrillation electrode 12, a ring electrode 14 and a tip electrode 16, each coupled to a conductor located within the lead body 10. Tines 18 are provided in maintaining electrode 16 in contact with the tissue of the right ventricle. Electrodes 16, 14 and 12 may correspond generally to conventionally available pacing and defibrillation electrodes.

The proximal end of the lead carries a connector assembly, beginning with a molded lead bifurcation 20, which splits off two of the conductors within lead body 10 to a bipolar, in-line connector assembly 24, generally corresponding to the IS-1 connector standard for pacing leads. However, other types of connector assemblies may also be adapted to practice the present invention. Connector assembly 24 is provided with a first set of sealing rings 28, a connector ring 32, a second sealing ring 34 and connector pin 36. Connector pin 36 is coupled to the conductor which extends through the lead body 10 to tip electrode 16. Connector ring is coupled to the conductor which extends through the lead body 10 to ring electrode 14. The conductor coupled to defibrillation electrode 12 extends into connector assembly 22, which carries a set of sealing rings 26 and a connector pin 36, coupled to the conductor extending through lead body 10 to defibrillation electrode 12.

In the specific context of the lead illustrated in FIG. 1, the conductor coupling connector pin 36 to electrode 16 takes the form of a monofilar or multifilar coiled conductor to allow passage of a stylet therethrough, while the conductors coupling ring electrode 14 to connector ring 32 and coupling defibrillation electrode 12 to connector pin 30 take the form of bundled, stranded wires, provided with a coating of PTFE. However, the conductors coupling ring electrode 14 and defibrillation electrode 12 may take the form of any of the various conductor types known for use in conjunction with implantable electrical leads. If fewer electrodes are provided on the lead, correspondingly fewer conductors will be included. One or more physiologic sensors may be added to the lead or substituted for one or more of the illustrated electrodes. Also located within lead body 10 is a stranded wire conductor which extends along a length of the coiled conductor and which serves as a mechanism for bridging a fracture of the coiled conductor which occurs between the ends of the stranded conductor. In some embodiments, the stranded conductor also couples electrode 16 to connector pin 36, providing both an axial reinforcement and a redundant electrical connection, as described in more detail below. In other embodiments, the electrical interconnection between the coiled and stranded conductors may simply be the contact between the two conductors which occurs as a result of both conductors being located in the same lumen of the lead.

Figure 2:
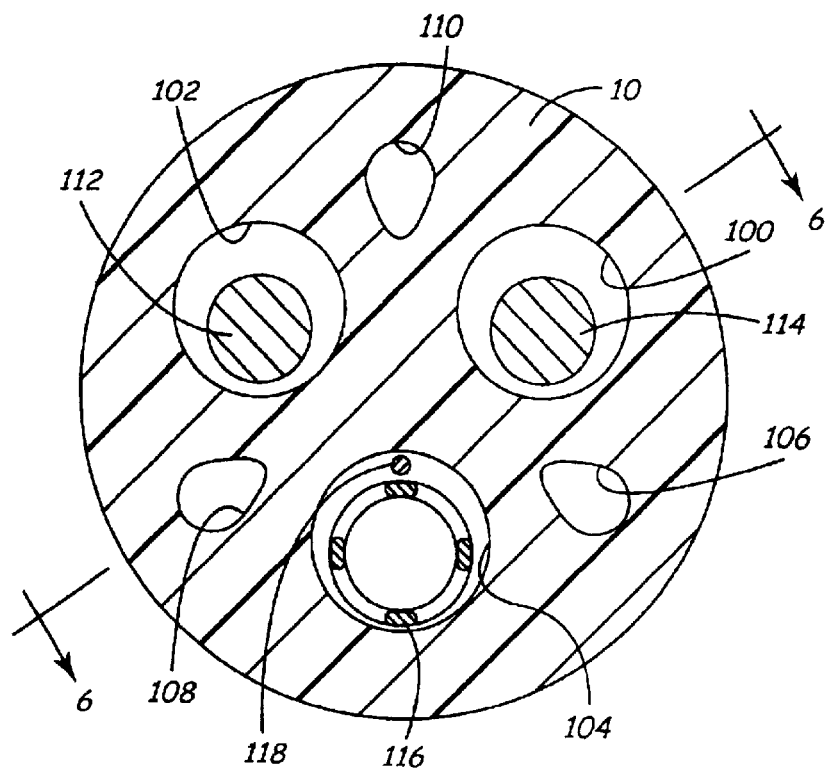
FIG. 2 is cross-sectional view through the lead of FIG. 1, illustrating a first embodiment of the invention.

FIG. 2 illustrates a cross-section through lead body 10, illustrating the inter-relation of the conductor lumens 100, 102 and 104 with compression lumens 106, 108 and 110, which are described in more detail in U.S. Pat. No. 5,584,873, issued to Shoberg et al. and incorporated herein by reference in its entirety. In this view it can be seen that lumens 100 and 102 contain conductors 112 and 114, which in the illustrated embodiment may take the form of PTFE coated bundled stranded wires having a generally straight configuration. In particular, conductors 112 and 114 may take the form of a PTFE coated, bundled, stranded 49 filar cable formed of seven strands, each strand formed of seven filars, as described in more detail in U.S. Pat. No. 5,584,873 by Shoberg et al. incorporated herein by reference in its entirety. Lumen 104 contains a conventional multifilar coiled conductor 116 and a small diameter bundled stranded wire conductor 118. Conductor 118 may take the form of a seven filar bundle or cable of MP35N or silver cored MP35N wire, as described in U.S. Pat. No. 5,246,014, issued to Williams et al and also incorporated herein by reference in its entirety, such that conductor 118 corresponds generally to one of the seven strands that make up conductors 112 and 114. In preferred embodiments, conductor 118 may have an outer diameter of about 0.003 inches.

In spite of its small diameter and generally straight configuration, stranded conductor 118 is extremely resistant to fracturing in response to repeated flexure of the lead body and displays a high tensile strength. Thus, should coil conductor 116 fracture, redundant, stranded conductor 118 will remain to provide for connection to the electrode to which coiled conductor 116 is coupled. If the stranded and coiled conductors are uninsulated from one another, they make contact with one another at multiple points along the lead body, so that a break of the coiled conductor occurring between the ends of the stranded conductor will be bridged. The ends of conductor 118 may also be mechanically coupled to the coiled conductor 116 and thereby serve to maintain the structural integrity of the lead, preventing partial disassembly due to applied tensile forces. If the lead is removed, conductor 118 may thus also serve as a reinforcement, allowing traction force to be applied to the distal end of the lead during extraction. In either case, conductor 118 allows for continued functioning of the lead after fracture of the coiled conductor 116, allowing for replacement of the lead, when convenient, without interruption of the therapeutic function of the pacemaker or stimulator to which the lead is coupled.

In some embodiments of the invention, conductor 118 is uninsulated along its length and thus makes contact with conductor 116 at various points along the length of the lead. In such embodiments, it is to be expected that the conductor 118 will serve as both a redundant conductor, coupling the connector pin 36 to the electrode 16, and as a conductive bridge between the broken ends of the conductor 116, as it will be in contact with the conductor 116 on either side of the break. With this structure, changes in overall impedance between the connector pin and electrode are expected to be relatively small, allowing for essentially undiminished performance of the lead. Alternatively, conductor 118 may be provided with an insulative coating of PTFE or other insulative material. In such embodiments, conductor 118 will serve as a redundant connector, connecting connector pin 32 to electrode 16, and upon fracture of conductor 116, a substantial change in connector pin to electrode impedance will be manifested. In the context of implantable stimulators capable of monitoring changes in lead impedance, this provides the physician and/or the device itself with a mechanism for detecting the fracture in 116. However, within the context of the present invention, the fracture can be detected without the serious consequences which would otherwise be associated with disconnection of the electrode 16 from the connector pin 36. In the context of implantable stimulators having the ability to automatically adjust stimulus pulse amplitude and input amplifier sensitivity, the device may respond to the change in lead impedance by noting the occurrence of a fracture in conductor 116 and may correspondingly alter its programmed parameters in order to restore performance essentially to that preceding the fracture of conductor 116.

Figure 3:
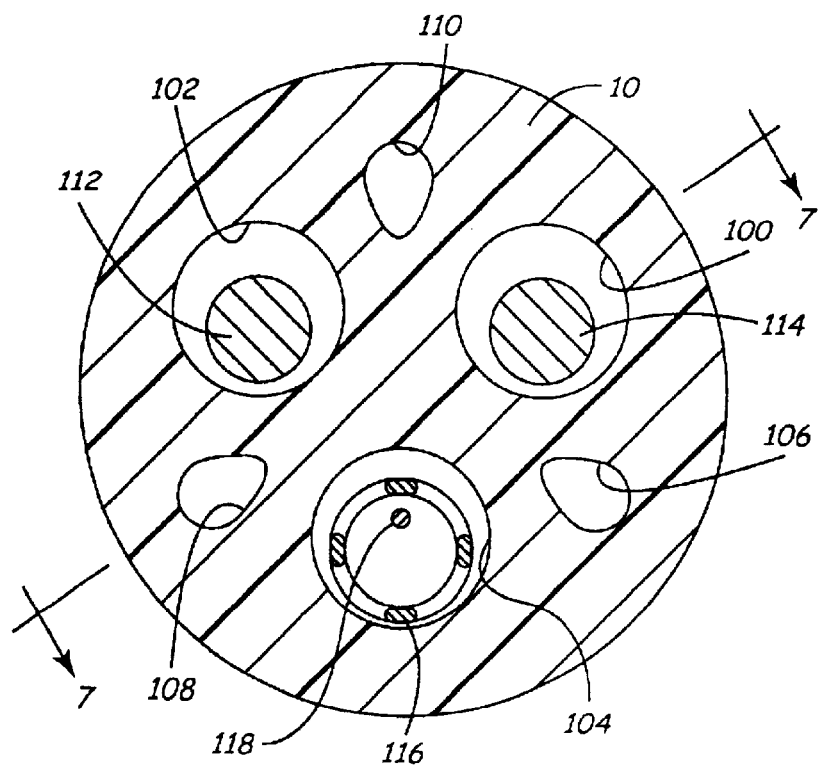
FIG. 3 is cross-sectional view through the lead of FIG. 1, illustrating a second embodiment of the invention.

FIG. 3 is a cross-sectional view through an alternative embodiment of the lead illustrated in FIG. 1, in which all labeled elements correspond to identically labeled elements in FIG. 2. The embodiment illustrated in FIG. 3 differs from that illustrated in FIG. 2 only in that stranded conductor 118 is located within the lumen of conductor 116, rather than external to conductor 116. This embodiment may be particularly advantageous in the context of leads, such as epicardial electrode leads or some nerve and muscle stimulation leads which do not require passage of a stylet through the lumen of coil conductor 116.

Figure 4:
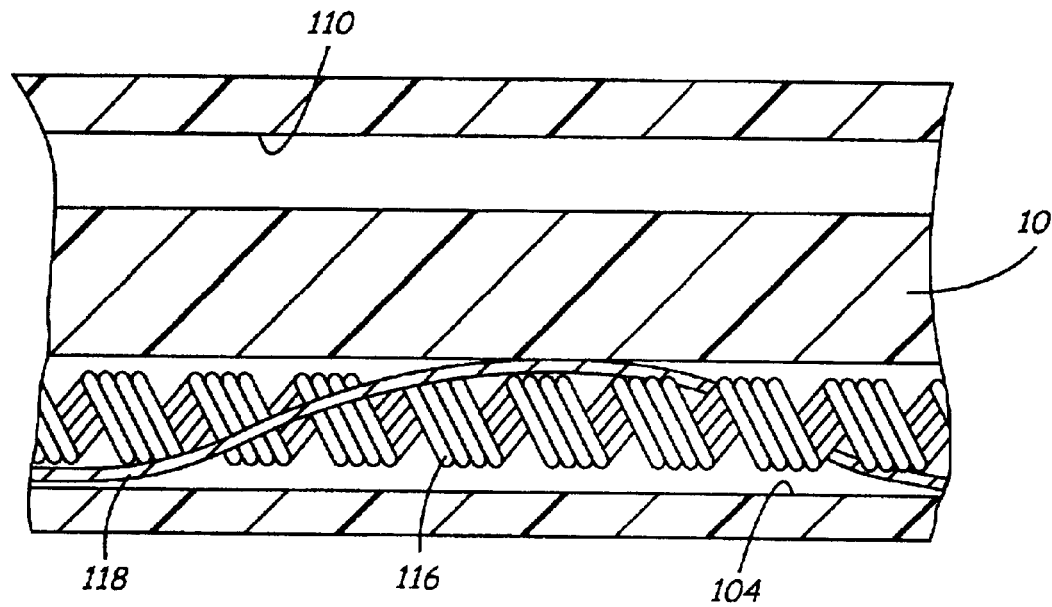
FIG. 4 is a side, cut-away view through the lead of FIG. 1, illustrating the first embodiment of the invention.

FIG. 4 is a side, cut-away view through the lead of FIG. 1, illustrating the first embodiment of the present invention, also illustrated in FIG. 2. In this view, it can be seen that stranded conductor 118 is loosely spiraled around coiled conductor 116 along the length of the lead, facilitating flexure of the lead body and the conductors located therein. If the ends of conductor 118 are mechanically coupled to conductor 116, this structure also allows for a limited amount of axial elongation of the lead body and conductor 116 along the length of conductor 118. All other labeled elements correspond to those illustrated in FIG. 2.

Figure 5:
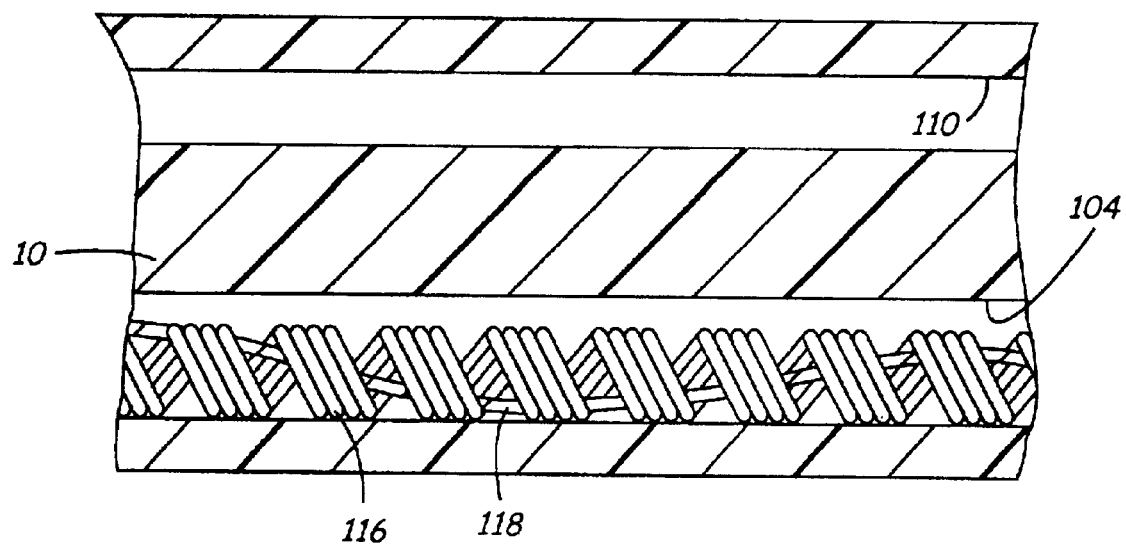
FIG. 5 is a side, cut-away view through the lead of FIG. 1, illustrating the second embodiment of the invention.

FIG. 5 shows a side cut-away view through the second embodiment of the lead of FIG. 1, also illustrated in FIG. 3. In this view, the stranded conductor is shown arranged loosely within the lumen of coiled conductor 116. All other labeled elements correspond to those illustrated in FIG. 2.

In the embodiments illustrated in FIGS. 2, 3, 4 and 5, conductor 118 may be insulated or uninsulated, as discussed above, depending on whether contact between the two conductors along their length is desired. An alternative embodiment in which the stranded conductor is desired to be insulated from the coiled conductor along some portion of its length may employ a separate lumen in the lead body for the stranded conductor, intermediate its points of connection to the coiled conductor. An additional alternative as discussed below may employ a tubular, insulative sheath within or around coiled conductor 116 to insulate it from conductor 118.

FIG. 6 et seq. show basic mechanisms which may optionally be employed to mechanically interconnect the stranded conductor 118, the coiled conductor 116, electrode 16 and connector pin 36. These illustrated interconnection mechanisms are intended to be exemplary, and may of course, be employed in conjunction with other components of implantable leads, including other types of electrical connectors such as connector rings, corresponding to connector ring 32 and to interconnect these conductors with other types of electrodes and to interconnect these components with other lead components such as physiologic sensors such as pressure sensors, oxygen sensors, temperature sensors and the like.

FIG. 6 is a sectional view through the distal portion of the lead illustrated in FIG. 1. In this view, the interconnection of conductor 116, conductor 118 and electrode 16 is visible. Extending distally from the defibrillation electrode 12, the lead takes the form of a molded piece part 228, which carries ring electrode 14, which is in turn coupled to stranded conductor 112 (not visible in this view). Electrode 16 as illustrated is a steroid-eluting electrode, provided with a monolithic controlled release device 222 located within a chamber within the electrode. Electrode 16 is coupled to a coiled conductor 116 and 118 by means of an external crimping sleeve 224, which compresses conductor 118 against conductor 116 and compresses conductor 116 against the proximal portion 220 of electrode 16. Other types of tip electrodes, including screw-in electrodes may of course be substituted for electrode 16. Similarly, other mechanisms may be employed to interconnect conductors 118 and 116 and electrode 16, including welding, swaging, crimping and combinations thereof, including mechanisms disclosed in commonly assigned U.S. Pat. No. 5,676,694 to Boser et al. granted Oct. 14, 1997, and U.S. Pat. No. 6,026,567 granted Feb. 22, 2000, incorporated herein by reference in there entirety.

Conductor 114 passes through an internal lumen 100 within lead body 10, and has its insulation removed in areas in which it passes through the cross-bore crimp sleeve 212. The distal turn of electrode coil 12 can be seen at 12A as it passes through the perpendicular cross-bore through sleeve 212. The sleeve 212 is crimped to the conductor 114 and a portion of the distal turn of electrode coil 12 is inserted through the cross bore and the entry and exit points of the coil are laser welded to the sleeve. External polymeric sleeve 230 is slid over the distal ends of conductor coil 12, and the areas between the sleeve 230 lead body 10 is backfilled by means of medical adhesive or other polymeric material. The electrode coil 12 may be secured to the outer circumference of the lead body 10 by means of a backfilling process as described in U.S. Pat. No. 4,934,049, incorporated herein by reference in its entirety.

FIG. 7 illustrates the distal portion of the lead in the second embodiment of the invention in which the stranded conductor 118 is located internal to coil conductor 116. All illustrated elements correspond to identically numbered elements in FIG. 6, with the exception that a bore is provided in the proximal section 220A of electrode 16, and stranded conductor 118 is crimped therein.

While FIGS. 6 and 7 show the inter-connection of the stranded and coiled conductors at the tip electrode 16, these conductors may instead be connected at a point proximal to the tip electrode, for example by use of a cross-bore crimp sleeve similar to sleeve 212, or by means of other types of welded, swaged or crimped connections as discussed above.

Figure 8:
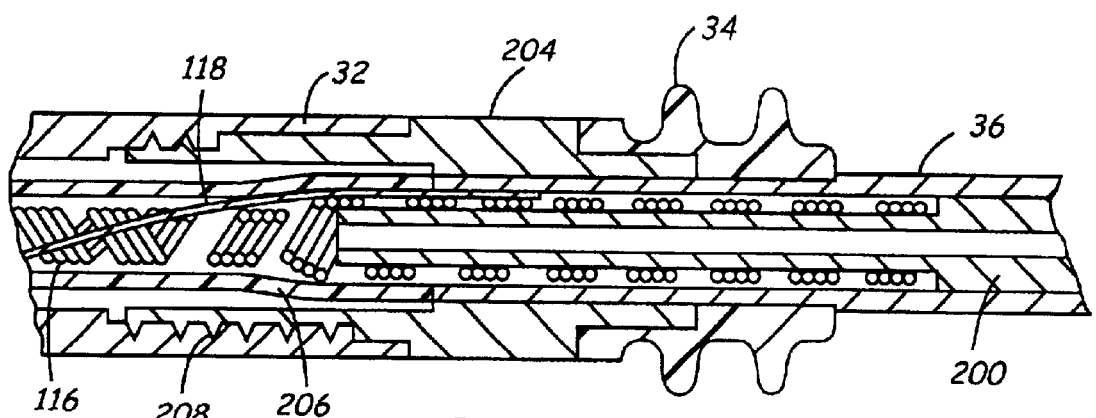
FIG. 8 is a side, cut-away view through the connector assembly of the lead of FIG. 1, illustrating the first embodiment of the invention.

FIG. 8 is sectional view through the bipolar connector assembly 24 of the lead illustrated in FIG. 1, depicting the first embodiment of the invention. In this view, the proximal end of connector pin 36 is visible in cross-section, and connector ring 32 is visible in cross-section. Connector pin 36 is coupled to coiled conductor 116 by means of a swaging core 200, which compresses conductor coil 116 and stranded conductor 118 between the interior lumen of connector pin 36 and the outer surface of swaging core 200, in a conventional fashion. An insulative sleeve 206 surrounds conductors 116 and 118, and extends distally, back through the connector assembly into molded sealing ring sleeve 28 (FIG. 1).

Surrounding connector pin 36 is a molded sealing ring sleeve 34, which may be fabricated of silicone rubber, which in turn is mounted to a spacer 204 which is typically fabricated of a harder plastic, such as polyurethane. Spacer 204 is molded in situ between connector pin 36 and ring electrode 32, and is maintained in mechanical interconnection with electrode 32 by means of internal threading 208, as described in U.S. Pat. No. 4,572,605, issued to Hess, et al., incorporated herein by reference in its entirety.

Figure 9:
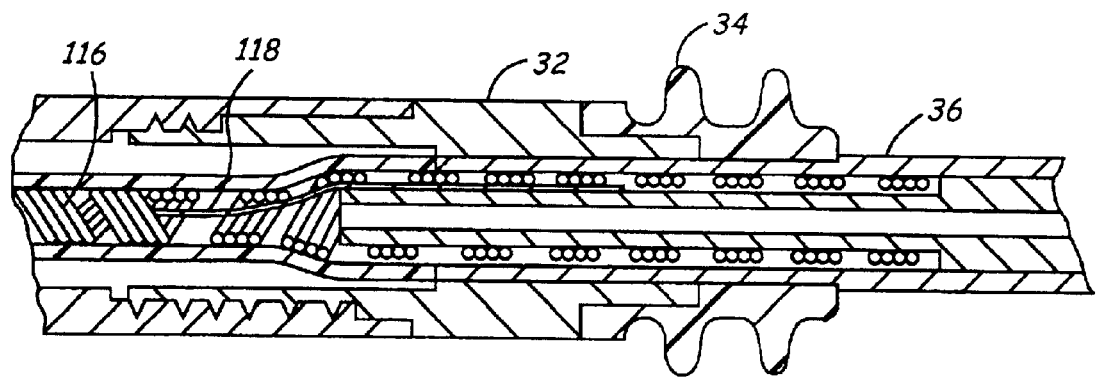
FIG. 9 is a side, cut-away view through the connector assembly of the lead of FIG. 1, illustrating the second embodiment of the invention.

FIG. 9 is a sectional view through the bipolar connector assembly 24 of the lead illustrated in FIG. 1, illustrating the second embodiment of the invention. All illustrated elements correspond to identically numbered elements in FIG. 8, with the exception that the stranded conductor 118 is located internal to coil conductor 116.

As in the case of FIGS. 6 and 7 above, other mechanisms may be employed to interconnect conductors 118 and 116 and connector pin 36, including welding, swaging, crimping and combinations thereof, as described above. Additionally, these conductors may instead be connected at a point distal to the connector pin, for example by use of a cross-bore crimp sleeve similar to sleeve 212, or by means of other types of welded, swaged or crimped connections as discussed above.

If it is not desired to mechanically interconnect one or both ends of the stranded conductor 118 to the coiled conductor 116, the internal structure of the leads may correspond to those illustrated in FIGS. 6, 7, 8 or 9 above, with the exception that the stranded conductor 118 is simply not crimped, swaged or otherwise coupled to the connector pin, electrode or coiled conductor 118. In such embodiments, the stranded conductor may extend the entire length of the coiled conductor or may extend over only a portion of the length of the coiled conductor. While FIGS. 6, 7, 8 and 9 illustrate the coil and stranded conductor pair coupled to the connector pin and tip electrode, it should also be understood that the invention may also be usefully practiced in leads in which these conductors are coupled to other connector elements, other electrodes, and/or physiologic sensors located on the lead body. The interconnection methods of FIGS. 6, 7, 8 and 9 may also be used to connect the stranded conductor 118 to the coiled conductor 116 and to such other lead components.

Figure 10:
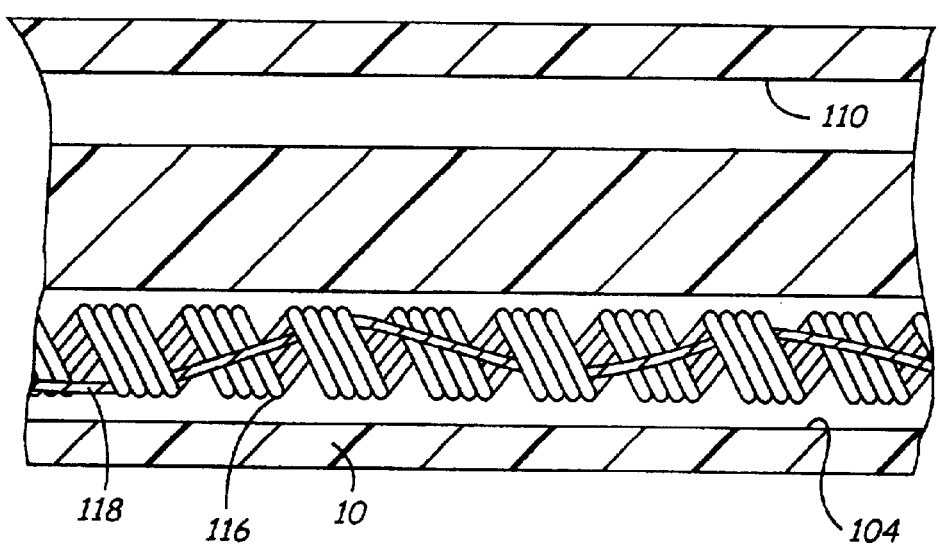
FIG. 10 is a side, cut-away view through the lead of FIG. 1, illustrating a third embodiment of the invention.

FIG. 10 illustrates a third embodiment of the invention. All numbered components correspond to identically numbered components in the Figures above. In this embodiment, an uninsulated stranded conductor 118 repeatedly enters and exits the internal lumen of the coiled conductor 116, by passing between the coils. This embodiment, while more difficult to assemble, provides for in increase in the number of contact points between the stranded and coiled conductors, which may be beneficial in the case of coil fractures as it will in many cases shorten the distance which the stranded conductor must bridge as compared to the first and second embodiments and may provide for more consistent contacts between the stranded and coiled conductors.

Figure 11:
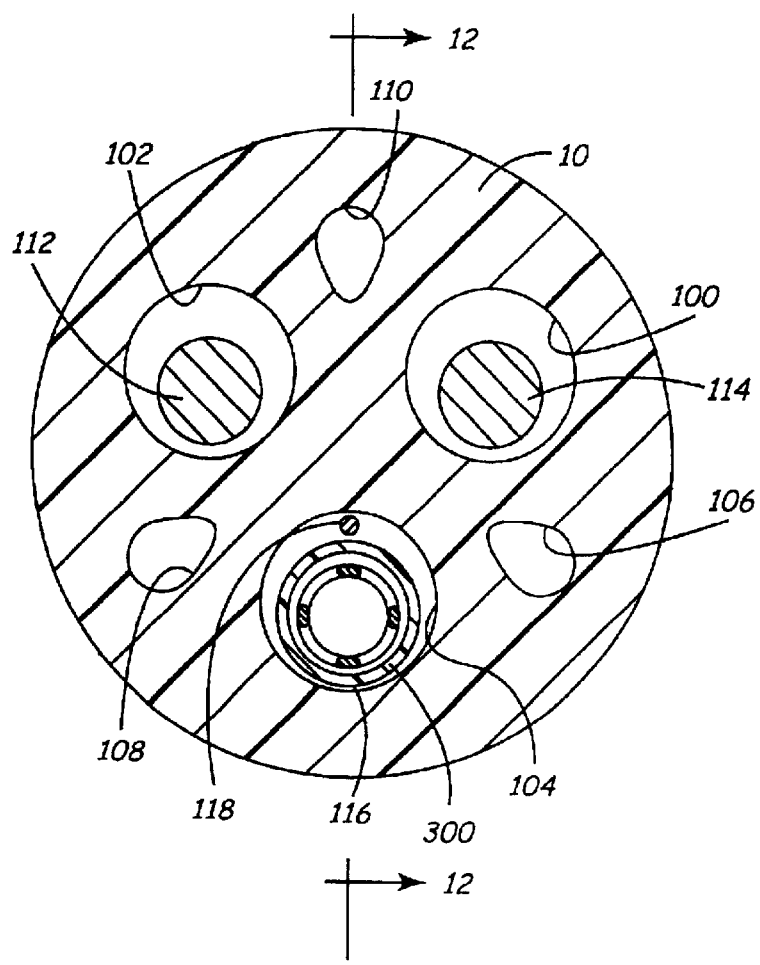
FIG. 11 is cross-sectional view through the lead of FIG. 1, illustrating a fourth embodiment of the invention.

FIG. 11 illustrates a cross section through a fourth embodiment of the invention. All numbered components correspond to identically numbered components in the Figures above. In this embodiment the stranded conductor 118 is located outside of coiled conductor 116 and is insulated from conductor 116 over at least a portion of its length by means of an insulative tube 300, located exterior to conductor 116. Tube 300 may be formed of PTFE or other insulative biocompatible plastic, and may extend over all or some of the length of coiled conductor 116. In this embodiment, it is desirable that the ends of stranded conductor 118 are mechanically coupled to the coiled conductor 116 on either side of the tube 300.

Figure 12:
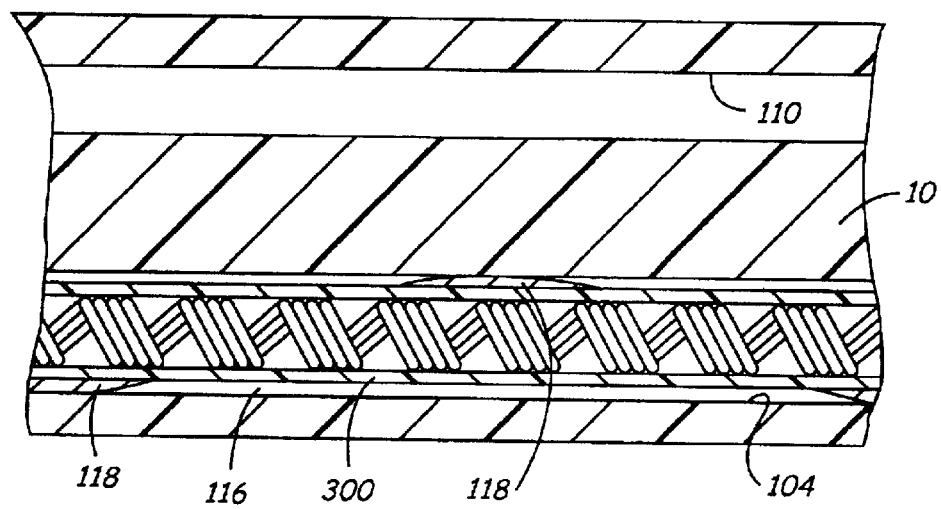
FIG. 12 is a side, cut-away view through the lead of FIG. 1, illustrating the fourth embodiment of the invention.
Figure 13:
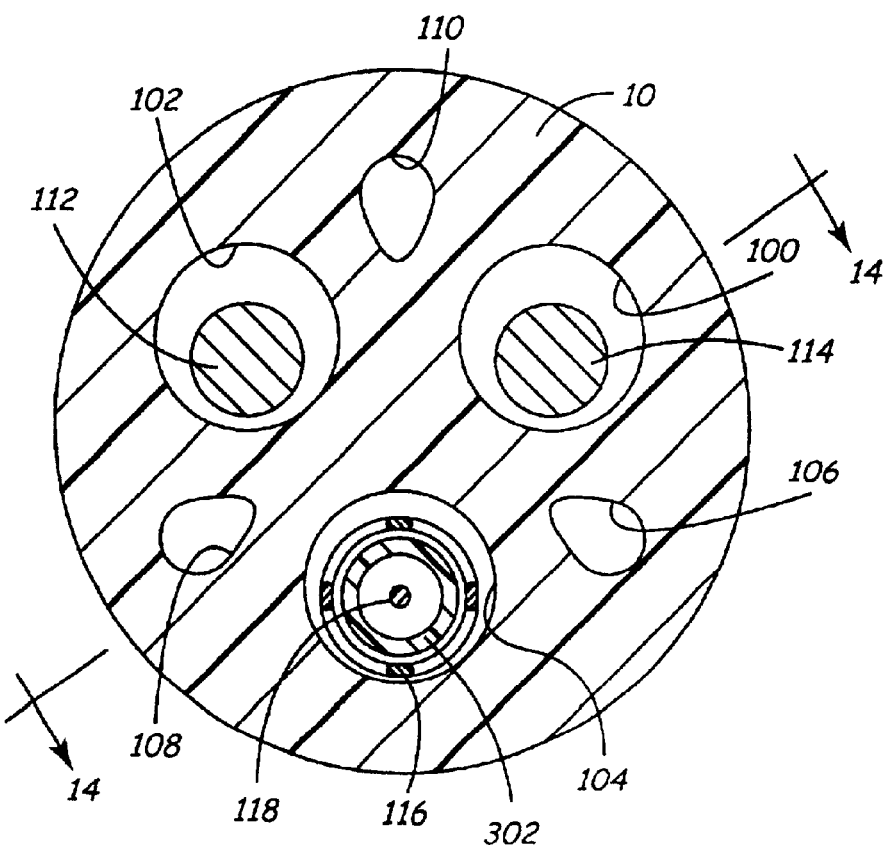
FIG. 13 is cross-sectional view through the lead of FIG. 1, illustrating a fifth embodiment of the invention.

FIG. 12 illustrates a side, cut-away view through the fourth embodiment of the invention as illustrated in FIG. 11. All numbered components correspond to identically numbered components in the Figures above FIG. 13 illustrates a cross section through a fifth embodiment of the invention. All numbered components correspond to identically numbered components in the Figures above. In this embodiment the stranded conductor 118 is located inside of coiled conductor 116 and is insulated from conductor 116 over at least a portion of its length by means of an insulative tube 302, located interior to conductor 116. Tube 302 may be formed of PTFE or other insulative biocompatible plastic, and may extend along all or some of the length of coiled conductor 116. In this embodiment, it is desirable that the ends of stranded conductor 118 are mechanically coupled to the coiled conductor 116 on either side of the tube 302.

Figure 14:
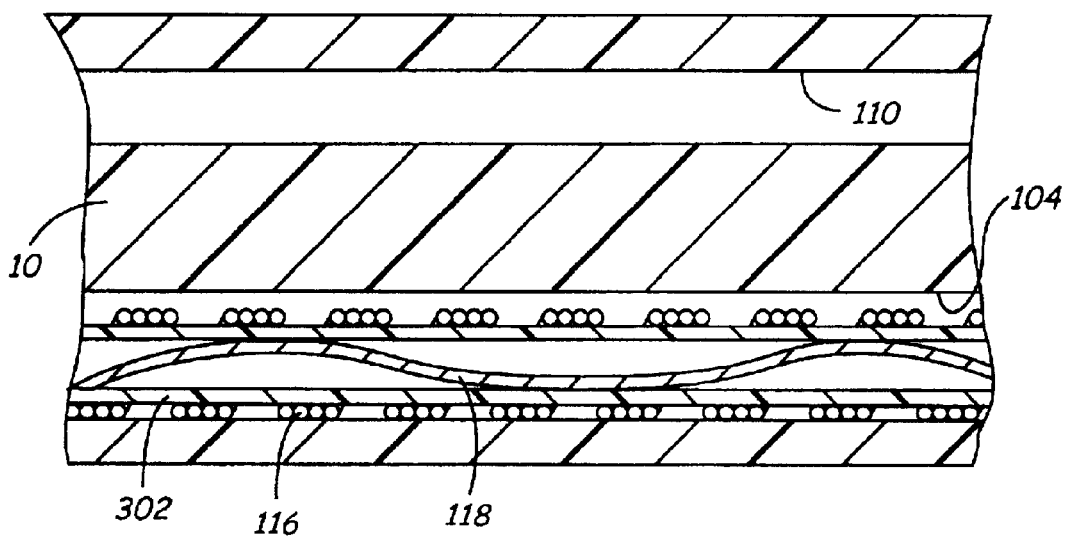
FIG. 14 is a side, cut-away view through the lead of FIG. 1, illustrating the fifth embodiment of the invention.

FIG. 14 illustrates a side, cut-away view through the fifth embodiment of the invention as illustrated in FIG. 13. All numbered components correspond to identically numbered components in the Figures above.

FIG. 15 illustrates an alternative mechanism for interconnecting a stranded conductor 412 with a coiled conductor 416, both located within an internal lumen of lead body 410. Conductive crimp sleeve 418 is crimped to coiled conductor 416 by crimps 420. Optionally, a cylindrical crimping core (not illustrated) may be inserted into the lumen of coiled conductor 416, prior to crimping. Stranded conductor 412 is coupled to the crimp sleeve 418 by means of conductive sleeve 422, by the following methods. Stranded conductor 412 may be threaded through sleeve 422, which is then pushed onto crimping core 418, pulling stranded conductor 412 along and compressing it between crimp sleeve 418 and sleeve 422. In conjunction with this method, the interior of sleeve 422 may be provided with threads or other internal texturing to frictionally engage stranded conductor 412. Alternatively, stranded conductor 412 may be arranged alongside crimp core 418 and sleeve 422, which may then be pushed onto crimp core 418, compressing conductor 412 between crimp sleeve 418 and sleeve 422. In conjunction with this method, the exterior of crimp of sleeve 418 may be provided with threads or other external texturing to frictionally engage stranded conductor 412. As yet another alternative, sleeve 422 may simply be crimped around stranded conductor 412 and crimping sleeve 418. Crimp sleeve 418 may take the form of a portion of a connector pin or ring on the proximal end of the lead body or a portion of an electrode or other sensor on the distal portion of the lead body, or may simply be a cylindrical sleeve, employed to couple the stranded and coiled conductors at some point along the lead body. Plastic sleeve 414 insulates stranded conductor 412 from coiled conductor 416 over a portion of their lengths.

FIG. 16 is a plan view of a defibrillation lead in which the present invention is practiced, employing a tip electrode taking the form of a rotatable fixation helix 316. The lead of FIG. 16 is provided with an elongated insulative lead body 310, preferably fabricated of silicone rubber, polyurethane or other biocompatible elastomer. At the distal end of the lead, it carries an elongated defibrillation electrode 312, a ring electrode 314 and a rotatable helical tip electrode 316, rotatably and advancably mounted in insulative electrode head 318. Each electrode is coupled to a conductor located within the lead body 310. Electrodes 314 and 312 may correspond generally to conventionally available pacing and defibrillation electrodes. A cap member 319 is located at the distal end of electrode head 318 and serves to retain a monolithic controlled release device as discussed below.

The proximal end of the lead carries a connector assembly, beginning with a molded lead bifurcation 320, which splits off two of the conductors within lead body 310 to a bipolar, in-line connector assembly 324, generally corresponding to the IS-1 connector standard for pacing leads. However, other types of connector assemblies may also be adapted to practice the present invention. Connector assembly 324 is provided with a first set of sealing rings 328, a connector ring 332, a second set of sealing rings 334 and connector pin 336. Connector pin 336 is rotatably mounted and is coupled to a rotatably mounted conductor that extends through the lead body 310 to helical electrode 316. Connector ring 332 is coupled to a conductor which extends through the lead body 310 to ring electrode 314. A conductor coupled to defibrillation electrode 312 extends into connector assembly 322, which carries a set of sealing rings 326 and is coupled to connector pin 336.

In the specific context of the lead illustrated in FIG. 16, the conductor coupling connector pin 336 to electrode 316 takes the form of a monofilar or multifilar coiled conductor to allow passage of a stylet therethrough, while the conductors coupling ring electrode 314 to connector ring 332 and coupling defibrillation electrode 312 to connector pin 330 take the form of bundled, stranded wires, provided with a coating of PTFE. However, the conductors coupling ring electrode 314 and defibrillation electrode 312 may take the form of any of the various conductor types known for use in conjunction with implantable electrical leads. If fewer electrodes are provided on the lead, correspondingly fewer conductors will be included. One or more physiologic sensors may be added to the lead or substituted for one or more of the illustrated electrodes. Also located within lead body 310 is a stranded wire conductor which extends along a length of the coiled conductor and which serves a mechanism for bridging a fracture of the coiled conductor which occurs between the ends of the stranded conductor, as discussed above.

Figure 17:
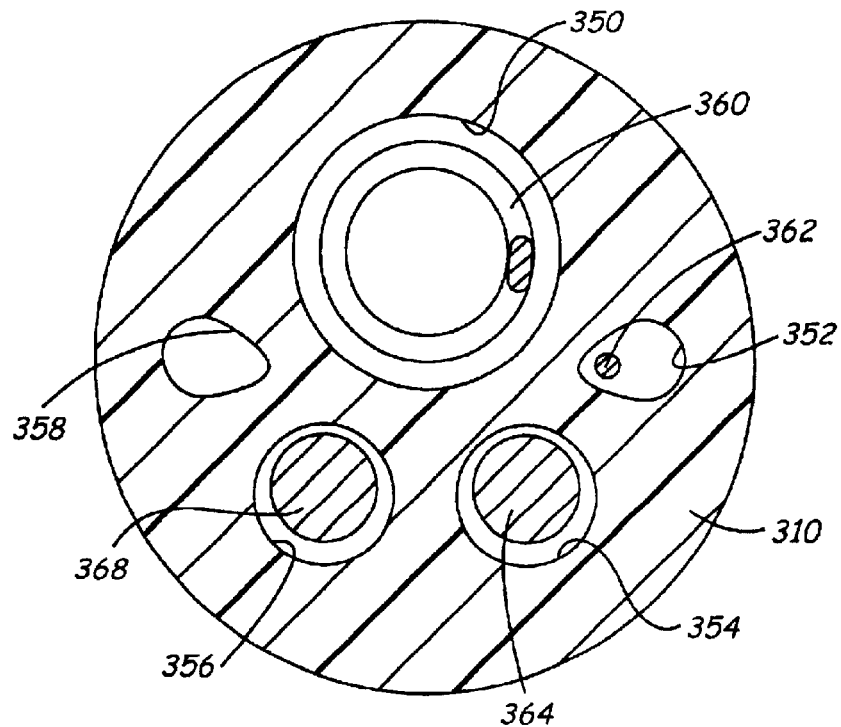
FIG. 17 is a cross-sectional view through the lead of FIG. 16.

FIG. 17 illustrates a cross section through the lead illustrated in FIG. 16. The lead body is provided with five lumens, including three circular lumens 350, 354 and 356 and two teardrop-shaped compression lumens 352 and 358. Coiled conductor 360 is coupled to helical electrode 316 (FIG. 16) and connector pin 336 (FIG. 16). On rotation of connector pin 336, conductor 360 transmits torque to rotate electrode 316, advancing it out the distal end of electrode head 318 (FIG. 16) and screwing it into heart tissue. Conductors 364 and 368 as illustrated are stranded or cabled conductors corresponding to conductors 112 and 114 (FIG. 2) and couple connector pin 330 to defibrillation electrode 312 and connector ring 332 to electrode 314, respectively. Stranded conductor 362 is coupled to coiled conductor 360 adjacent the proximal and distal ends of the lead, providing a redundant connector and tensile reinforcement in the same fashion as conductor 118 (FIG. 2) discussed above. The wall of lead body 310 separating lumens 350 and 352 insulates conductor 362 from conductor 360 between the points at which they are electrically coupled. Electrical interconnection of conductors 360 and 362 is by means of rotating electrical couplings as described in conjunction with FIGS. 18 and 19 below, which allow rotation of coil conductor 360 relative to stranded conductor 362.

Figure 18:
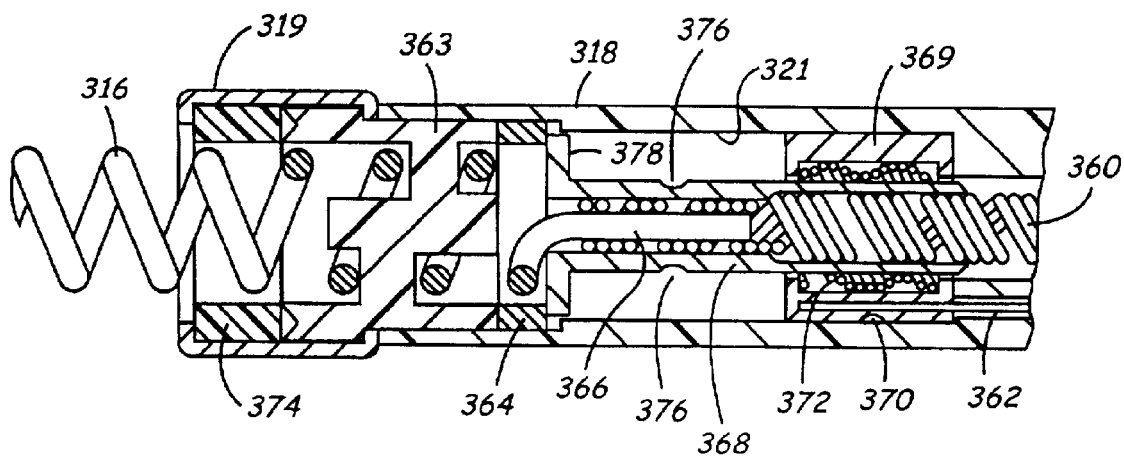
FIG. 18 is a side, cut-away view through the distal portion of the lead of FIG. 16.

FIG. 18 is a side cut-away view through the distal portion of electrode head 318 of the lead of FIG. 16. Electrode head 318 is fabricated of a rigid, biocompatible plastic such as a polyurethane, and is provided with an internal longitudinal lumen 321. Cap 319 retains a toroidal monolithic controlled release device 374, which serves to elute an anti-inflammatory steroid such as sodium dexamethasone phosphate, as described in U.S. Pat. No. 4,972,848, issued to DiDomrnico and incorporated herein by reference in its entirety. Guide 363 engages helical electrode 316 such that rotation of the electrode serves to advance it out the distal end of electrode head 318 or withdraw it into lumen 321. Coiled conductor 360 is mechanically and electrically coupled to the proximal end of electrode 316 by conductive crimp sleeve 368, compressed by crimps 376. Crimp sleeve 368 is provided with a circumferential shoulder 378 which serves to limit distal movement of helix 316 by contact with radio-opaque marker ring 364 and which serves to limit proximal movement of helix 316 by contact with conductive ferrule 369.

Electrical interconnection of stranded conductor 362 and coiled conductor 360 is accomplished by ferrule 369 which is crimped to stranded conductor 362 by crimp 370 and is provided with contact means 372 for coupling to conductive crimp sleeve 368. As illustrated the contact means 372 is a conductive spring with individual turns offset from one another to springingly contact both ferrule 369 and crimp sleeve 368 while allowing rotation and longitudinal movement of crimp sleeve 368, in a manner analogous to that illustrated in U.S. Pat. No. 4,557,643, incorporated herein by reference in its entirety. Alternatively, coupling means in the form of other types of spring contacts, fine wire brushes or other known mechanisms for rotatable electrical couplings may be substituted.

Figure 19:
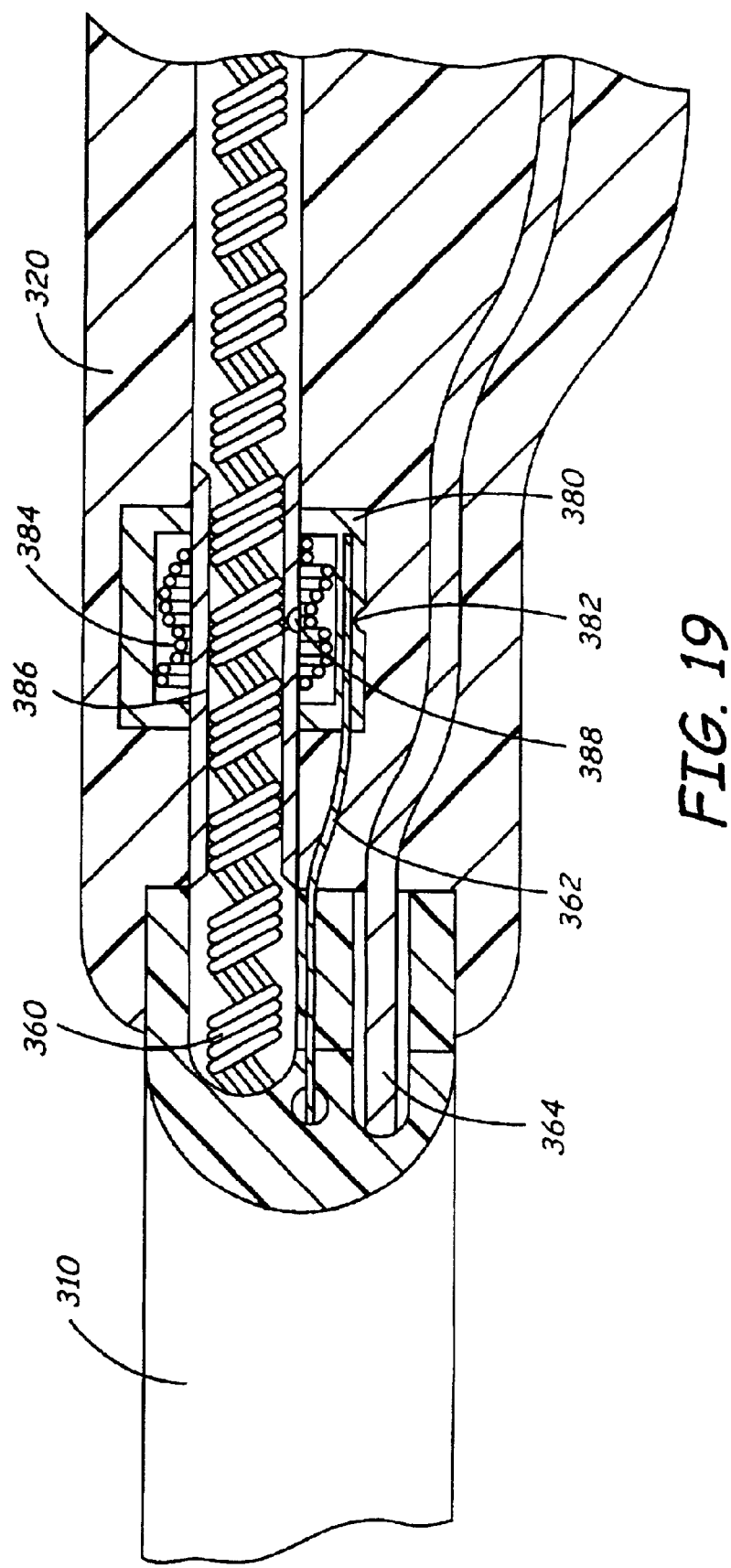
FIG. 19 is a side, cut-away view through the proximal portion of the lead of FIG. 16.

FIG. 19 shows a side, cut-away view through the lead of FIG. 16 in the vicinity of bifurcation 320. In this view, coiled conductor 360 and stranded conductors 362 and 364 are visible, exiting from lead body 310 and entering into molded bifurcation 320. Interconnection of stranded conductor 362 and coiled conductor 360 is accomplished by ferrule 380 coupled to conductor 362 by crimp 382. Crimp sleeve 386 is coupled to coiled conductor 360 by crimps 388 and conductive spring 384. These components function in the same way as their counterparts illustrated in FIG. 18 to couple the conductors while allowing rotational movement of coiled conductor 360. As in the case of FIG. 18, the known mechanisms for making a rotating electrical connection may be substituted. While the rotatable coiled conductor in this embodiment is coupled to a helical electrode, it may alternatively be coupled to any other electrode which is deployed or manipulated by applied torque and may also be employed with any other mechanism requiring both applied torque and an electrical connection.

The foregoing embodiments of the current invention involve systems wherein a cable is provided to lend redundancy to a coil conductor. In another embodiment of the inventive system, a dual-cable system is utilized wherein a cable is used to provide redundancy to another cable.

Figure 20:
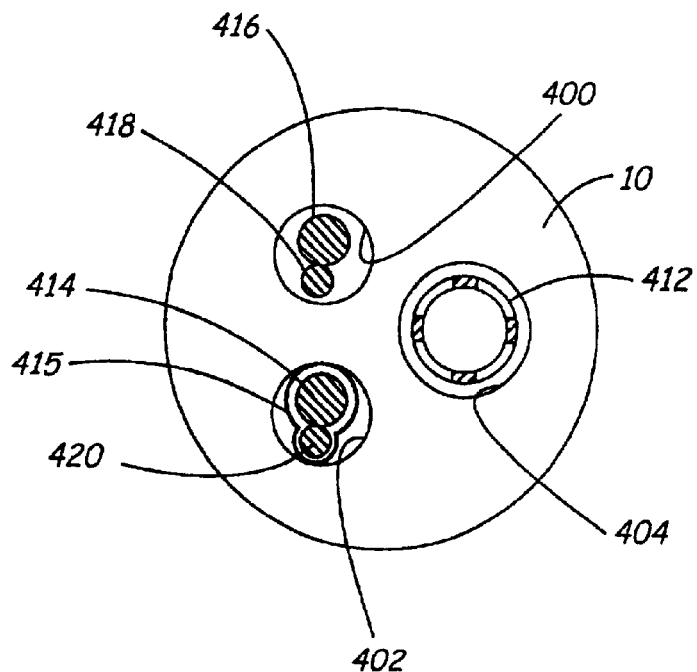
FIG. 20 is a cross-sectional view through the lead of FIG. 1 at line 2—2 illustrating an embodiment of the invention utilizing a dual cable system.

FIG. 20 is a cross-section view of another embodiment of the lead of FIG. 1 at line 2—2 employing a dual-cable system. The lead includes lumens 400, 402, and 404. Lumen 400 carries a high voltage conductor cable 416 that electrically couples shock electrode 12 to pin contact 30 of connector 22 (FIG. 1). A safety cable 418 is shown in lumen 400 adjacent to high voltage conductor cable 416. The safety cable may run substantially parallel to, or alternatively, may be wrapped about the conductor cable.

Similarly, lumen 402 carries a low voltage conductor cable 414. The low voltage conductor cable electrically couples ring electrode 14 to contact ring 32 of connector 24. A safety cable 420 may in lumen 402 to provide redundancy to conductor cable 414. This cable may run substantially parallel to, or be wrapped around, the conductor in the manner discussed above. Further, in this embodiment, the combination of the conductor cable 414 and safety cable are shown to be coated with a lubricious coating 415, which may be PTFE or ETFE. This coating, which may be employed along part, or all, of the cable-cable assembly, makes the cable assembly easier to insert within lumen 402. Such a coating could also be used with the cable assembly residing within lumen 400 if desired.

The sizes of the conductor cables are dictated largely by the particular desired application. In one embodiment, the diameter of the conductor cables may range from 0.006" to 0.018" and the diameter of the safety cables may range from 0.003" to 0.010" to minimize lead size. In another embodiment, the safety cables may be larger. The safety cables 418 and 420 may take any of the forms described above with respect to cable designs.

The lead of FIG. 20 further includes lumen 404, which houses a conductor coil 412. Conductor coil, which may be mono-filar or multi-filar, electrically couples the tip electrode 16 to the proximal pin 36 of connector 24. The lumen of coil 412 may serve as a passageway for a delivery stylet. In one embodiment, the inner diameter of the coil may range from approximately 0.015"–0.025" and the outer diameter from approximately 0.020–0.035".

In FIG. 20, safety cables 418 and 420 are not isolated from the conductor cables 416 and 414, respectively. Contact exists between each safety cable and its respective conductor cable substantially along the length of the lead. In the event of a fracture within the conductor cable, the associated safety cable provides backup electrical conduction so that lead failure does not occur.

Figure 21:
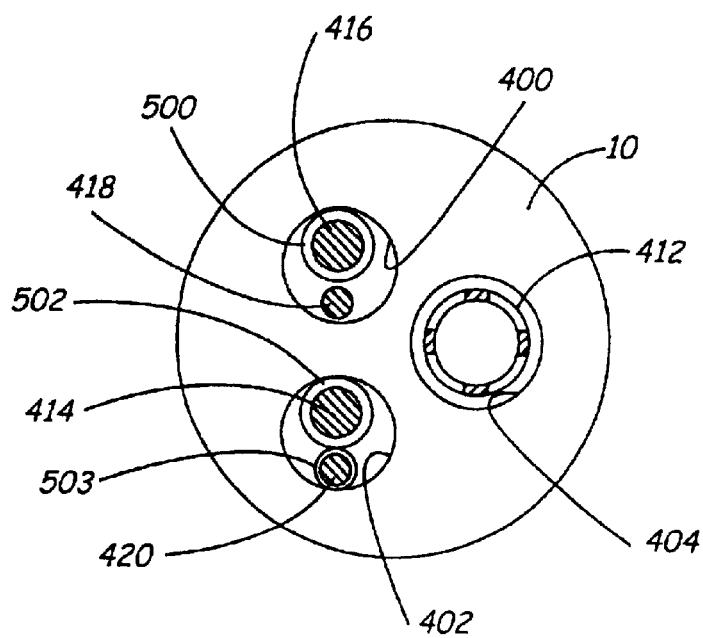
FIG. 21 is a cross-sectional view of another embodiment of the invention utilizing a dual cable system.

FIG. 21 is a cross-sectional view of another embodiment of the dual-cable design shown in FIG. 20. In this embodiment, safety cables 418 and 420 are isolated from the conductor cables 416 and 414 along at least a portion of the length of the conductor cable. This electrical isolation is provided by insulation coatings 500 and 502, respectively. The insulation coating may be silicone, a fluoro-polymer, or any bio-stable and biocompatible insulating polymer. In particular, conductor cables 416 and 414 may take the form of a PTIFE coated, bundled, stranded cable, formed in seven strands. Each strand may be formed of seven filars, as described in more detail in U.S. Pat. No. 5,584,873 by Shoberg et al. referenced above. A respective safety cable may run parallel to its conductor cable or may be wrapped about the conductor cable. One or more of the safety cables may be insulated in a manner similar to that shown for conductor cables 416 and 414. For example, safety cable 420 is shown surrounded by an electrically insulative layer 503. As will be appreciated by those skilled in the art, many alternative embodiments may be contemplated for the interface between the safety cables and the conductor cables, including intermittent use of insulation for the safety cable to provide predetermined electrical contact points between the cables.

The foregoing embodiment has advantages over an embodiment wherein the safety cable is not electrically isolated from its respective conductor. By isolating a safety cable, a failure in the conductor cable may be detected by a change in impedance when conduction is occurring only through the safety cable. Thus, the failure will be detected without signal loss, and a replacement procedure may be scheduled. As discussed above, an implantable device may automatically alter stimulation parameters to compensate for this detected change in impedance so that therapy is not compromised.

FIG. 22 is a side cut-away view of a portion of a lead according to FIG. 20. This view shows conductor cables 414 and 416 adjacent to their associated safety cables 420 and 418, respectively. A cross-groove crimp sleeve 430 electrically couples cables 416 and 418 to high-voltage coil electrode 12. More specifically, crimp sleeve 430 includes a tubular portion 434 that is slid over, and crimped to, conductor cable 416 and safety cable 418. Several filars of shock coil 12 are welded in the grooved tower 432 of the crimp sleeve to electrically and mechanically couple this structure to the coil. A crimp sleeve of this nature is described in U.S. Pat. No. 5,676,694 referenced above.

FIG. 23 is a side cut-away view of an alternative embodiment of the lead shown in FIG. 22. Crimp sleeve mechanically couples to conductor cable 416A, but does not mechanically couple to safety cable 418A. Both conductor cable 416A and safety cable 418A extend distally from crimp sleeve 430A, with the safety cable being wrapped around conductor cable 416A. Contact between the safety cable 118A and the crimp sleeve 130A by virtue of the proximity of these structures within lumen 400, in conjunction with the wrapped configuration, provide the primary electrical connection between the safety cable and the conductor cable.

Figure 24:
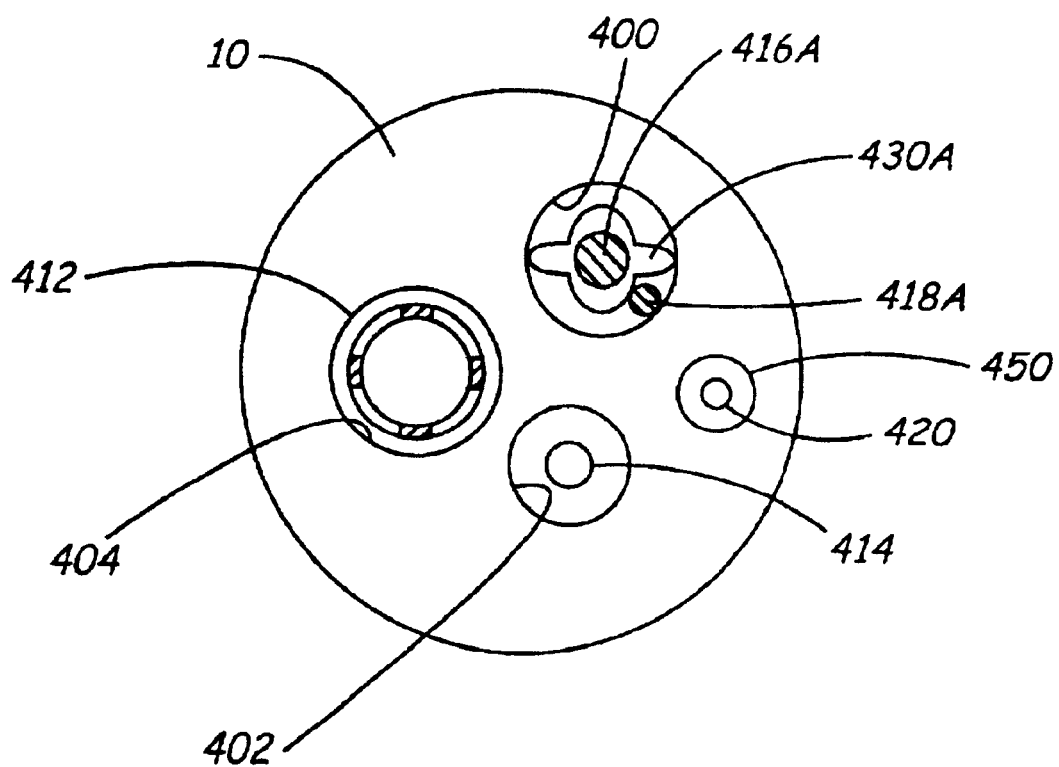
FIG. 24 is a cross-sectional view of the lead of FIG. 23 at line 24—24.

FIG. 24 is a cross-sectional view of the lead of FIG. 23 at line 24—24. This view shown the manner in which safety cable 418A by-passes crimp sleeve 430A. This manner also shows an embodiment wherein conductor cable 414 is electrically isolated from associated safety cable 420 along at least a portion of its length via an auxiliary lumen 450 in the manner discussed above with respect to FIG. 17 and the coil-cable design. In this embodiment, conductor cable 414 does not include insulation coating 502.

FIG. 25 is a partial side cut-away view of a dual cable design showing the interconnection of safety cable 420 and low-voltage conductor cable 414 at anode ring electrode 14. In this embodiment, anode ring electrode 14 includes an internal eyelet 441 that may be crimped to conductor cable 414 and safety cable 420. It should be noted that other types of joints, such as a weld or a press fit, may be employed to join the conductor cable 414 to the anode ring electrode 14.

FIG. 26 is a partial side cut-away view of a dual cable design showing an alternative mechanism for interconnecting safety cable 420A and low-voltage conductor cable 414A at anode ring electrode 14. Safety cable 420A bypasses eyelet, and both conductor cable 414A and safety cable 420A extend distal to the anode ring electrode 14. Safety cable 420A may be wrapped about the conductor cable 420A. This wrapped configuration forms the primary electrical connection between the safety cable and the conductor cable.

Figure 27:
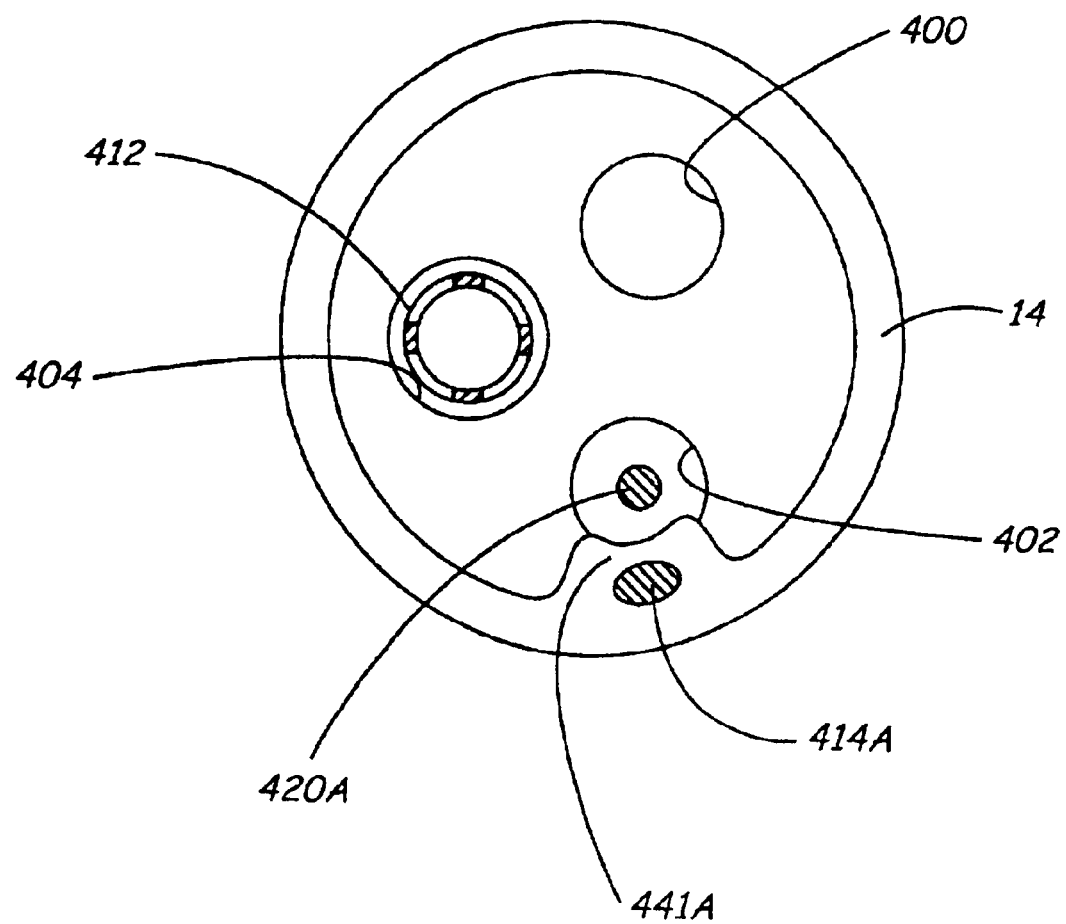
FIG. 27 is a cross-sectional view of the lead of FIG. 26 at line 27—27.

FIG. 27 is a cross-sectional view of the lead of FIG. 26 at line 27—27. This view shown the manner in which safety cable 414A by-passes eyelet 441A.

Figure 28:
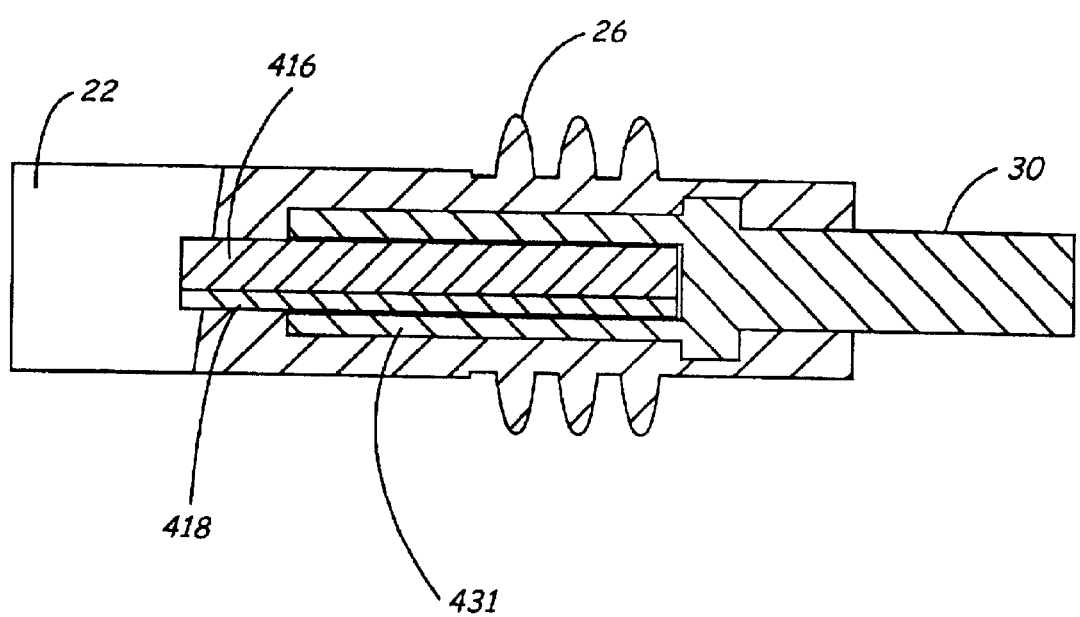
FIG. 28 is a partial side cut-away view of a high voltage connector illustrating the junction of the conductor cable and the safety cable.

FIG. 28 is a partial side cut-away view of high voltage connector 22 (FIG. 1) illustrating the junction of conductor cable 416 and safety cable 418. These cables are shown crimped within bore 431 of contact pin 30, although it will be understood that any other joining mechanism known in the art may be used in the alternative, including swaging, staking, or welding.

FIG. 29 is a side cutaway view illustrating a mechanism for coupling conductor cable 414 to safety cable 420 within the bifurcation sleeve 20 (FIG. 1). Coil 412 exits lead body 10 into insulation tubing 504 of the bifurcation sleeve 20. The insulated coil passes through the central bore of a junction component 520, and electrically couples to connector pin 36 (FIG. 1). In one alternative embodiment, this coil may transition to a cable within the bifurcation sleeve, with the cable being coupled to connector pin 36. This alternative embodiment is useful when fixation tines, rather than a helix, are provided at the lead distal end.

As discussed above, coil 412 is coupled to junction component 520. At the distal end of the junction component 520 is a smaller offset bore 522 into which safety cable 420 and the conductor cable 414 may be staked. A coil 516 is welded or crimped to the proximal end of junction component 520. In this configuration, coil 516 electrically couples conductor cable 414 and safety cable 420 to ring contact 32 (FIG. 1) of low voltage connector 24 through the junction component 520. The transition from a cable to a coil within the low voltage connector 24 increases the stiffness of the connector leg to aid in insertion of the connector into a connector cavity of an implantable medical device.

FIG. 30 is a side cutaway view illustrating another mechanism for coupling conductor cable 414 to safety cable 420 within the bifurcation sleeve 20. In this embodiment, conductor cable 414 and safety cable are both directly coupled to the contact ring 32. The two cables are staked within an offset bore 433 at the proximal end of the contact ring 32. It should be noted that other types of cable joints such as a weld or a press fit may be employed. Conductor coil 412, which is electrically coupled to tip electrode in the manner described above, passes through a central bore of the contact ring 32 to pin contact 36 (FIG. 1). Conductor coil 412 is shown surrounded by insulation tubing 504. As an alternative to coupling conductor cable 414 to safety cable 420 within the bifurcation sleeve 20, 414 can pass through the bifurcation sleeve 20 without such coupling.

Without such bifurcation coupling, the safety cable can pass outside of junction component 520 and then touch the conductor cable 414 on both sides of the junction component 520. The safety cable 420 and the conductor cable 414 continues to loosely lay up against each other as they pass both distally and proximally away from the junction component 520.

One option for the safety cable 420 to pass outside of junction component 520 is for the safety cable to pass through a PTFE or ETFE tube. This tube would be inside the bifurcation sleeve 20, would pass next to the junction component 520, and lead to the conductor cable 414 on both sides of the junction component 520.

Another option for the safety cable 420 to pass outside of junction component 520 is for the safety cable to lay in back filling material next to the junction component 520. The safety cable 420 would lead to the conductor cable 414 on both sides of the junction component 520.

If the junction component 520 joins the conductor cable 414 on one or both sides of the junction component 520 to the coil 412, also on one or both sides junction component 520, there is a need for the safety cable 420 to connect the conductors. That is, the safety cable 420 passes outside of the junction component 520 and inside of the bifurcation sleeve 20 and then loosely lays up against the coil 412 and/or the conductor cable 414 as they pass distally and/or proximally away from the junction component 520. In this way, if there is a fracture of the coil conductor 412 and/or the cable conductor 414, the safety cable 420 lays loosely next to the fracture in both the distal and proximal directions. With the safety cable 420 touching the fractured conductor (412 and/or 414) by loosely laying next to it in both the distal and proximal directions, the fracture is jumpered out.

On the ends of the safety cable can be a coupling method. One such coupling method is shown in FIG. 28. As an alternative to this, one or more of the safety cable 420 ends can remain without a coupling method.

On the end or ends of the safety cable 420 that are not coupled, one option is to leave them as is in the cut state. Other options involve forming the end by melting it into a more round shape. Other options involve putting medical adhesive on the melted or non-melted ends so as to make the end or ends less sharp. Other options involve bond tubes made of silicone, polyurethane, PTFE, and/or ETFE on the end(s) of the safety cable 420.

As an overall option to figures such as FIG. 29, the safety cable 420 and associated components can go distally or they can be rotated to go proximally. Using FIG. 29 as an example of this rotation, with the bifurcation sleeve as shown, 520, 412, 504, 522, 420, 414, 504 and/or 516 can all be rotated 180 degrees. As a second example, conductive components of FIG. 30 can also function if rotated 180 degrees with or without rotating the non-conductive components 180 degrees.

As an alternative to coupling the safety cable 420 within the bifurcation sleeve 20, there can be separate holes in the junction component 520 for the safety cable 420 and the conductor cable 414.

In one application of this, the safety cable 420 would be taken out of the hole where it touches the conductor cable 414 in FIG. 29. The hole then would be downsized to fit only the conductor cable 414. Then a similar hold would allow the safety cable 420 to pass through the junction component 520 without a coupling action. Then with or without a PTFE or ETFE tubing going between the safety cable 420 hole ends and the conductor cable 414, the safety cable 420 goes from the junction component hole to a position next to the conductor cable 414.

FIG. 31 is a cut-away view illustrating one embodiment of a distal end of a unipolar implantable defibrillation lead in which the current invention may be practiced. The lead is comprised of an elongated lead body 550 that carries a conductor cable 554 within insulation tubing 556. Conductor cable 554 is coupled at a proximal end to a high-voltage connector (not shown in FIG. 31) similar to that described above in reference to FIG. 1. At the distal end of lead body 550, conductor cable 554 is electrically and mechanically coupled via a crimp to a weld core crimp sleeve 560. High-voltage coil 552 is mounted over the crimp zone 562, and is welded to a shoulder 564 of the crimp sleeve 560, thereby electrically coupling high-voltage coil 552 to conductor cable 554. An insulated tip 559 is formed over the end of crimp sleeve 560.

The lead of FIG. 31 further includes a safety cable 558 that may be electrically coupled at a proximal end to conductor cable 554 in a manner similar to that shown in FIG. 28. At the distal end of the lead, safety cable 554 is positioned between insulation tubing 556 and high-voltage coil 552, and may extend to crimp sleeve 560. Safety cable 554 may be substantially parallel with, or alternatively, may be wrapped around insulation tubing 556.

FIG. 32 is a cut-away view illustrating an embodiment of a distal end of a bipolar, coaxial implantable lead in which the current invention may be practiced. The lead is comprised of an elongated lead body 570 that carries a conductor cable 582 within an inner insulation tubing 580. Conductor cable 582 is electrically coupled to tip electrode 590 at the distal end of the lead, as may be accomplished using a crimp, weld, or any other mechanism. In FIG. 32, conductor cable 582 is crimped within a bore 592 of tip electrode 590. Conductor cable 582 further extends proximally to a bipolar connector that may be similar to connector 24 (FIG. 1). Tines 573 provide a means for holding tip electrode 590 in contact with the myocardium. Conductor cable 582 may be associated with a safety cable lying adjacent to the cable to provide redundancy in the manner discussed above with the high-voltage or ring electrodes.

The lead of FIG. 32 further includes a coil 574 positioned proximal to tip electrode 590. A safety cable 576 is positioned within the turns of coil 574, and provides redundancy to coil. In a manner similar to that described above, safety cable 576 may be positioned substantially parallel to insulated conductor cable 582, or alternatively, may be wrapped around insulation tubing 580 of conductor cable 582. Coil 574 extends proximally into a connector, which may be similar to that of connector 24 (FIG. 1). Coil may be insulated along most of its length, while being exposed along a predetermined portion 575 that serves as an anode. The length of exposed portion 575 may range from approximately 2 mm to 6 cm, depending on the application, with shorter lengths being more useful as low voltage anode for true bipolar pacing and sensing in conjunction with the tip electrode and longer lengths being more useful as a shock coil that may double as an anode for integrated pacing and sensing with the tip electrode.

Figure 33:
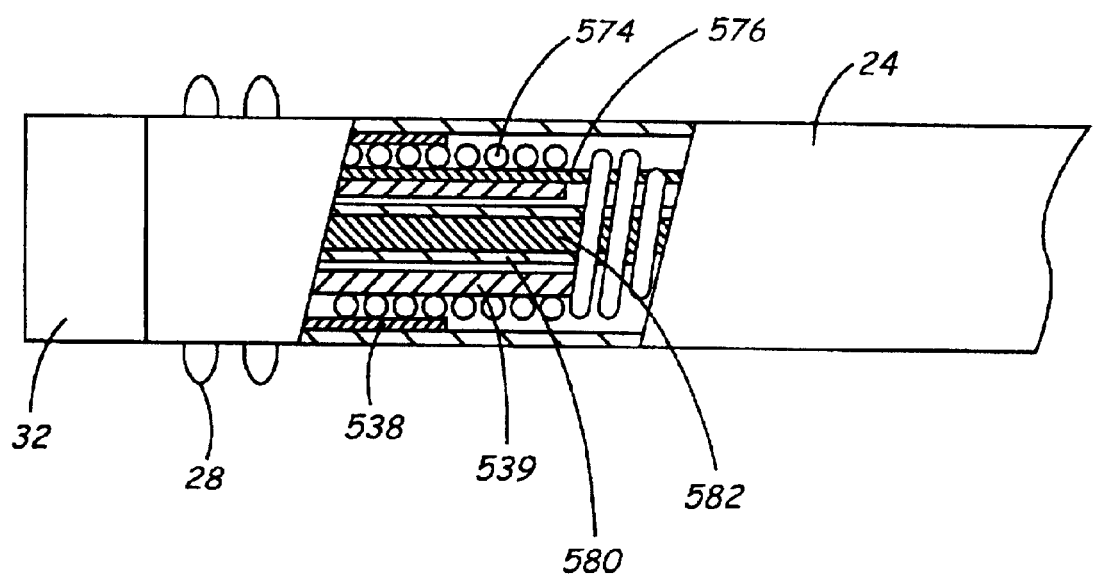
FIG. 33 is a cut-away view of one embodiment of a proximal termination of the outer coil and the safety cable of FIG. 32.

FIG. 33 is a cut-away view of one embodiment of a proximal termination of the outer coil 574 and the safety cable 576 of FIG. 32. The coil and cable are crimped between a core 539 and a distal portion of the ring contact 538. Ring contact 538 is electrically coupled to connector ring 32 (FIG. 1).

What is claimed is:

1. An implantable medical device (IMD) having an elongated body comprising:

an elongated conductor cable carried by the elongated body;

an electrical connector located at a proximal end of the elongated body and electrically coupled to the conductor cable;

a safety cable extended along at least a portion of the length of the conductor cable and being electrically coupled to the electrical connector and to the conductor cable at a first location and a second location distal to, and spaced from, the first location; and a coil conductor to electrically couple at least one of the safety cable and the conductor cable to the electrical connector.

2. The IMD of claim 1, and further including a junction component to mechanically and electrically couple the coil conductor to the safety cable and the conductor cable.

3. An implantable medical device (IMD) having an elongated body comprising:

an elongated conductor cable carried by the elongated body; and a safety cable extended along at least a portion of the length of the conductor cable end being electrically coupled to the conductor cable at a first location and a second location distal to, and spaced from, the first location;

an electrode coupled to a distal end of the elongated body and electrically coupled to the conductor cable and the safety cable; and a crimp sleeve to electrically couple at least one of the safety cable and the conductor cable to the electrode.

4. The IMD of claim 3, wherein the crimp sleeve is a cross-groove crimp sleeve.

5. An implantable medical device (IMD) having an elongated body comprising:

an elongated conductor cable carried by the elongated body; and a safety cable extended along at least a portion of the length of the conductor cable end being electrically coupled to the conductor cable at a first location and a second location distal to, and spaced from, the first location; an electrode coupled to a distal end of the elongated body and electrically coupled to the conductor cable and the safety cable; and wherein the electrode is an anode ring including an internal eyelet to crimp to at least one of conductor cable and safety cable.

6. An implantable medical device (IMD) having an elongated body comprising:

an elongated conductor cable carried by the elongated body; and a safety cable extended along at least a portion of the length of the conductor cable end being electrically coupled to the conductor cable at a first location and a second location distal to, and spaced from, the first location; an electrode coupled to a distal end of the elongated body and electrically coupled to the conductor cable and the safety cable; and wherein the electrode is selected from a group consisting of a high-voltage electrode, a ring electrode, and a tip electrode.

7. An implantable medical device (IMD) having an elongated body comprising:

an elongated conductor cable carried by the elongated body; and a safety cable extended along at least a portion of the length of the conductor cable end being electrically coupled to the conductor cable at a first location and a second location distal to, and spaced from, the first location;

wherein the safety cable is wound about the conductor cable.

8. An implantable medical device (IMD) having an elongated body comprising:

an elongated conductor cable carried by the elongated body; and a safety cable extended along at least a portion of the length of the conductor cable end being electrically coupled to the conductor cable at a first location and a second location distal to, and spaced from, the first location;

wherein at least a portion of the length of the safety cable between the first location and the second location is electrically isolated from the conductor cable.

9. The IMD of claim 8, wherein at least a portion of the length of the safety cable is surrounded by an electrically insulative material.

10. The IMD of claim 8, wherein the IMD includes first and second lumens to respectively carry at least a portion of the length of the safety cable and the conductor cable between the first and the second locations.

11. An implantable medical device (IMD) having an elongated body comprising:

an elongated conductor cable carried by the elongated body; and a safety cable extended along at least a portion of the length of the conductor cable end being electrically coupled to the conductor cable at a first location and a second location distal to, and spaced from, the first location;

wherein the conductor cable is a stranded cable.

12. The IMD of claim 11, wherein strands of the stranded cable include multiple filars.

13. An implantable medical device (IMD) having an elongated body comprising:

an elongated conductor cable carried by the elongated body; and a safety cable extending alongside an exterior of a portion of the conductor cable and being electrically coupled to the conductor cable at a first location and at a second location spaced apart from the first location.

14. The IMD of claim 13, further comprising a junction, component electrically and mechanically coupling the safety cable and the conductor cable at a one of the first location and the second location.

15. The IMD of claim 14, further comprising an electrode electrically coupled to the safety cable and the conductor cable by means of the junction component.

16. The IMD of claim 13, wherein the safety cable is wrapped about the conductor cable, to electrically couple the safety cable to the conductor cable, at a one of the first location and the second location.

17. The IMD of claim 13, wherein a portion of the safety cable between the first location end the second location Is electrically Isolated from the conductor cable.

* * * * *